United States Patent
Gillespie, III

(10) Patent No.: US 11,617,839 B2
(45) Date of Patent: Apr. 4, 2023

(54) SELF-RETRACTING MECHANIZED SYRINGE AND METHODS OF USE

(71) Applicant: Nspire Medical Technologies, LLC, Athens, TX (US)

(72) Inventor: Richard David Gillespie, III, Athens, TX (US)

(73) Assignee: Nspire Medical Technologies, LLC, Athens, TX (US)

( * ) Notice: Subject to any disclaimer, the term of this patent is extended or adjusted under 35 U.S.C. 154(b) by 0 days.

(21) Appl. No.: 17/579,222

(22) Filed: Jan. 19, 2022

(65) Prior Publication Data
US 2022/0134016 A1     May 5, 2022

Related U.S. Application Data

(62) Division of application No. 16/158,715, filed on Oct. 12, 2018, now Pat. No. 11,311,683.

(Continued)

(51) Int. Cl.
*A61M 5/32* (2006.01)
*A61M 5/20* (2006.01)
*A61M 5/31* (2006.01)

(52) U.S. Cl.
CPC .......... *A61M 5/322* (2013.01); *A61M 5/2033* (2013.01); *A61M 5/3245* (2013.01); *A61M 5/3148* (2013.01)

(58) Field of Classification Search
CPC .. A61M 5/322; A61M 5/2033; A61M 5/3245; A61M 5/3148

(Continued)

(56) References Cited

U.S. PATENT DOCUMENTS 5,271,744 A    12/1993   Kramer et al.
7,341,575 B2 *   3/2008   Rice .................. A61M 5/30
                                        604/72

(Continued)

FOREIGN PATENT DOCUMENTS

WO     2009081103 A1     7/2009

OTHER PUBLICATIONS

Amgen, Inc., Neulasta OnPro kit instructions, https://www.neulastahcp.com/neulasta-onpro/#, downloaded Aug. 6, 2019.

(Continued)

*Primary Examiner* — Phillip A Gray
(74) *Attorney, Agent, or Firm* — Stephen Y. Liu; Carstens, Allen & Gourley, LLP

(57) ABSTRACT

A self-retracting syringe has an injection assembly and a retraction assembly. The injection assembly has a housing, a spring rest, and a spring that is restrained initially in compression between the housing and the spring rest. A plunger rod is disposed inside the coil of the spring. A coupler in contact with the spring rest and the plunger rod releasably couples the plunger rod to the spring rest. When a latch is released, the plunger rod moves distally to urge a seal forward, which seal movement causes a hypodermic needle to extend and a medicament to be expelled through the hypodermic needle. A retraction assembly returns the hypodermic needle into the syringe body after the medicament is expelled. Embodiments of retraction assembly provide an inlet through which fluid may be introduced into the syringe through said hypodermic needle. Methods for filling the syringe are also described.

7 Claims, 38 Drawing Sheets

Related U.S. Application Data

(60) Provisional application No. 62/572,645, filed on Oct. 16, 2017.

(58) Field of Classification Search
USPC .......................................................... 604/135
See application file for complete search history.

(56) References Cited

U.S. PATENT DOCUMENTS

| | | |
|---|---|---|
| 9,707,356 B2 | 7/2017 | Hourmand et al. |
| 2010/0036319 A1* | 2/2010 | Drake ................... A61J 1/1406 29/428 |
| 2013/0218093 A1 | 8/2013 | Markussen et al. |
| 2013/0310759 A1 | 11/2013 | Hourmand et al. |

OTHER PUBLICATIONS

Enable Injections, Syringe Transfer System, https://enableinjections.com/technology/enfuse-on-body-plalform/syringe-transfer-system/, downloaded Aug. 6, 2019.
International Search Report, PCT/US2018/055802, dated Feb. 1, 2019, with written opinion.

* cited by examiner

SECTION I-I

SECTION II-II

SECTION III-III

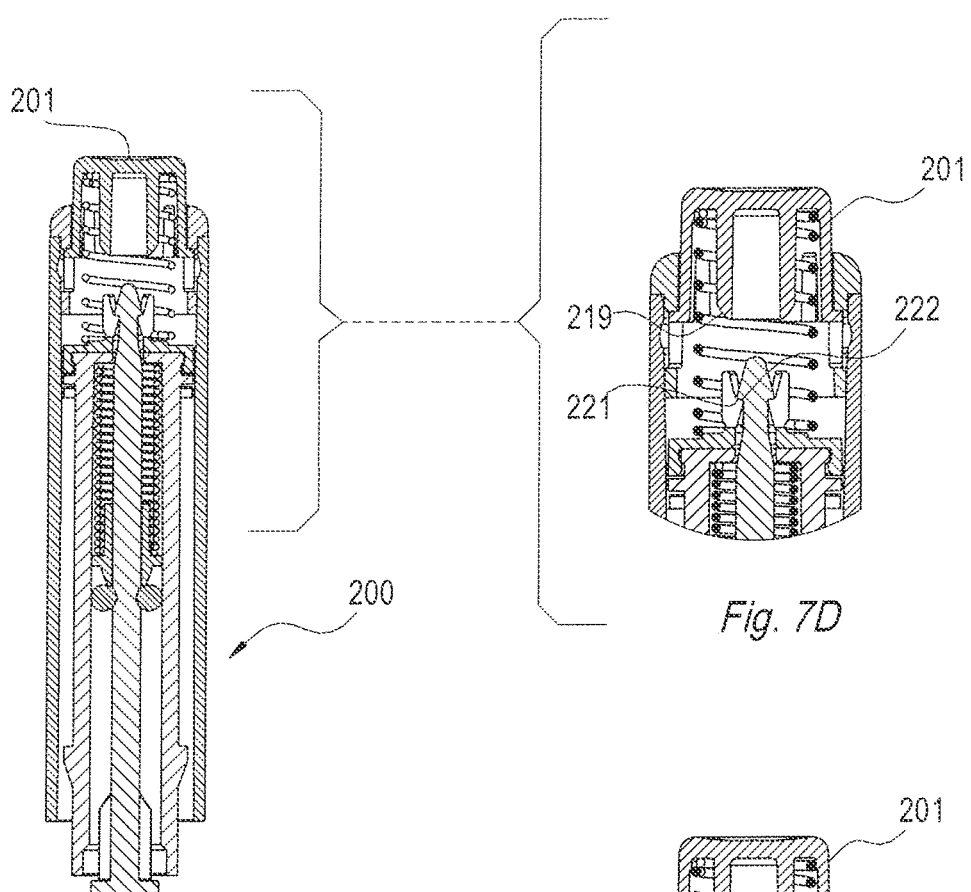
Fig. 7C
Fig. 7D
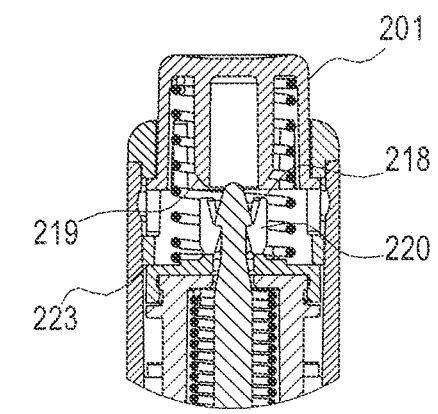
Fig. 7E
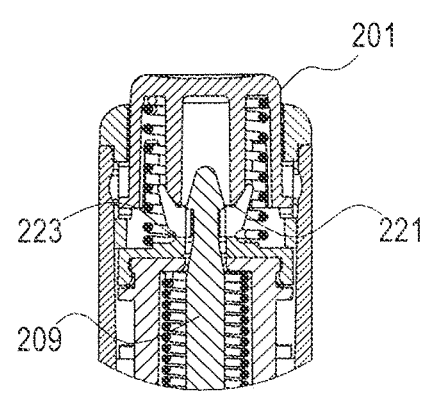
Fig. 7F

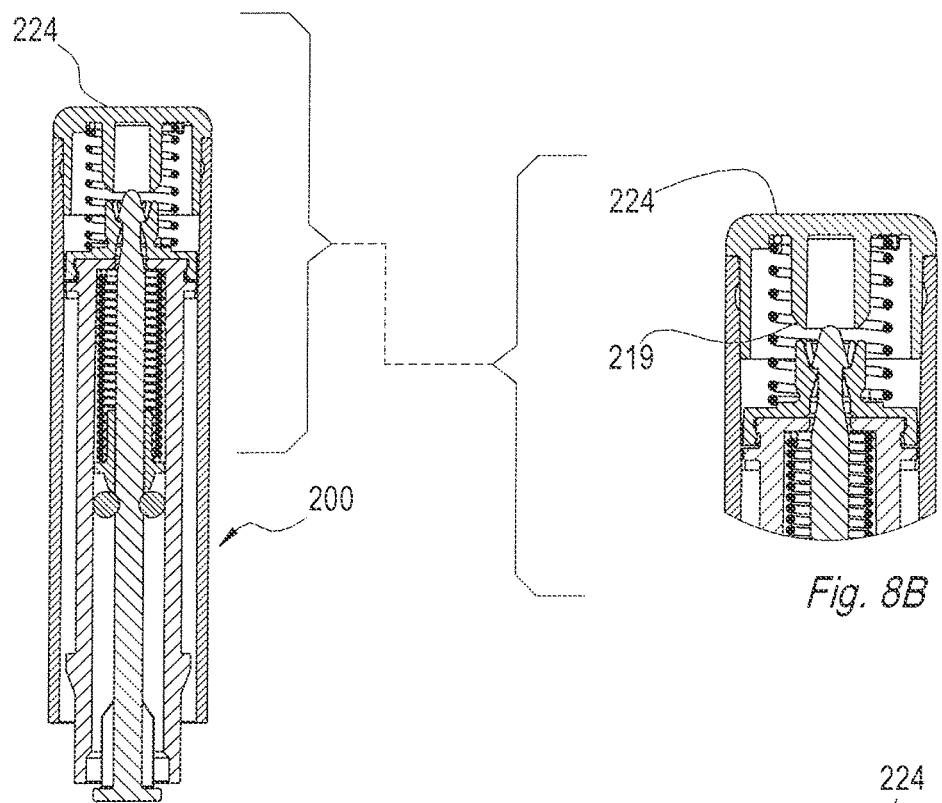
Fig. 8A
Fig. 8B
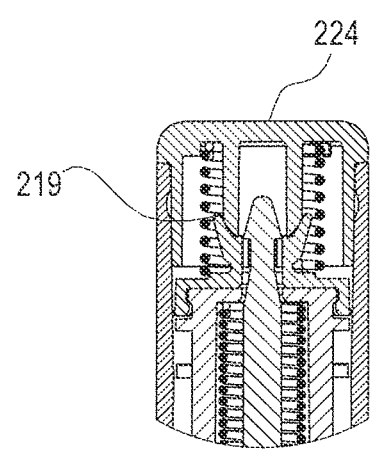
Fig. 8C

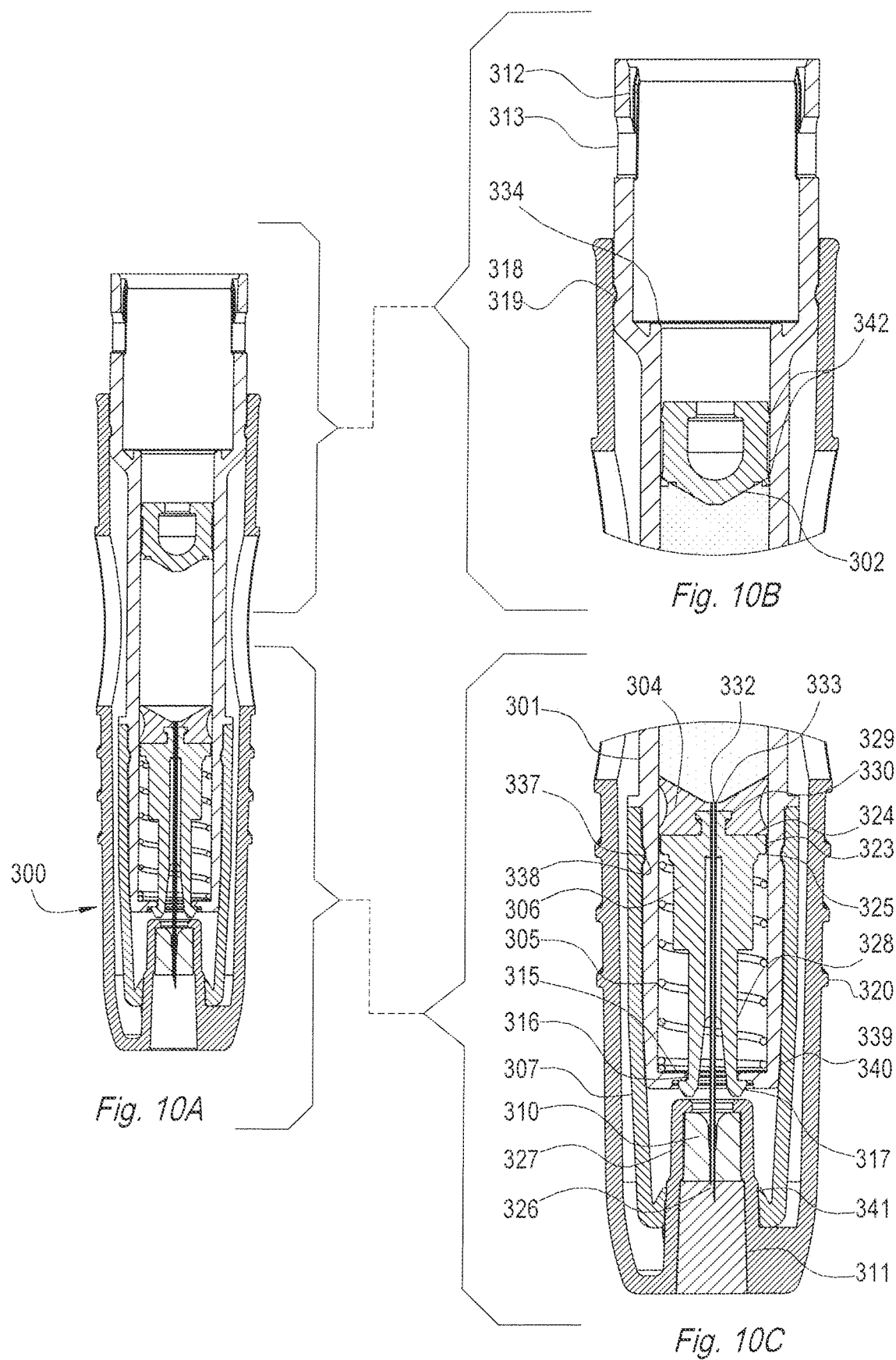

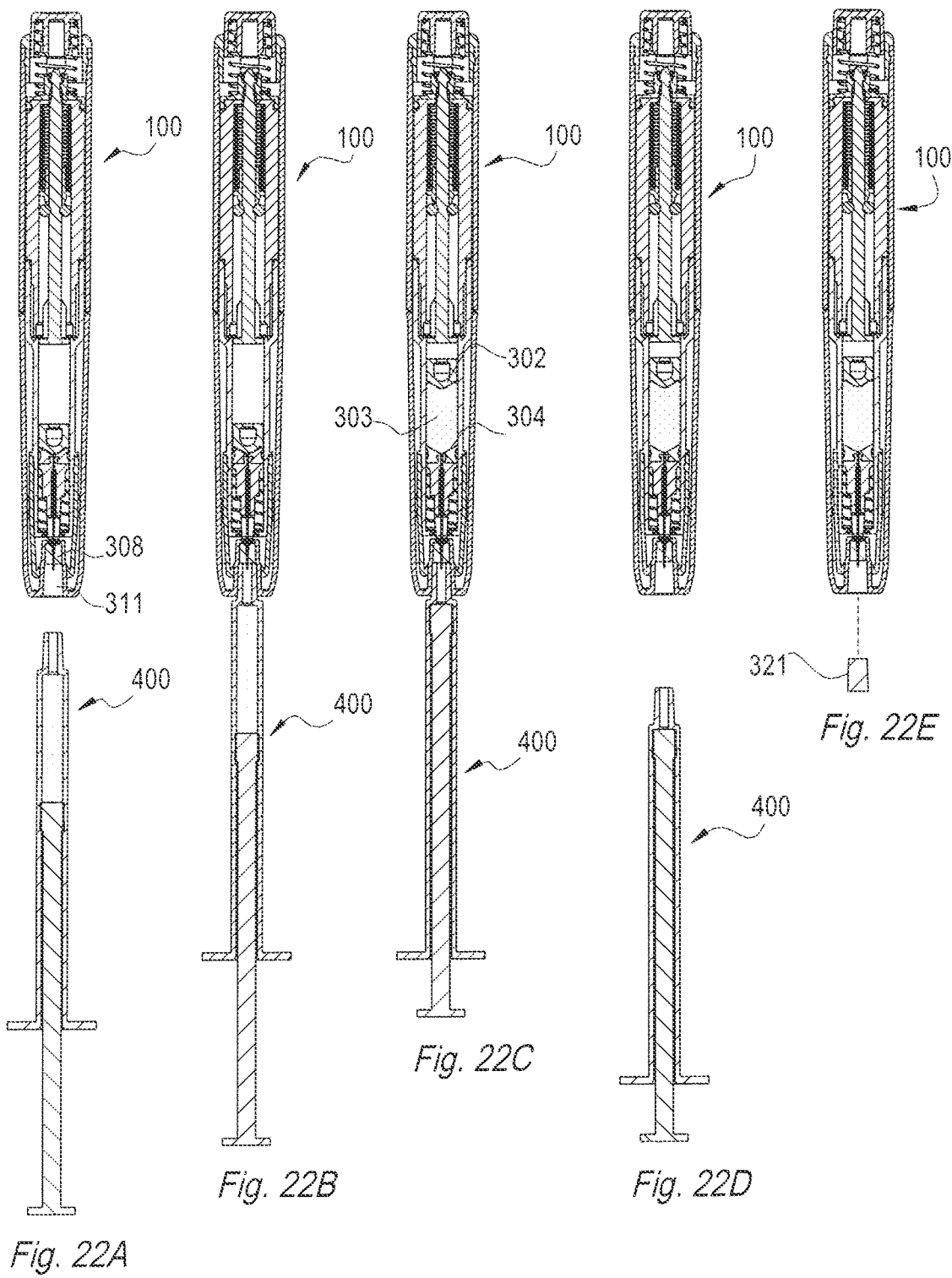

SECTION IV-IV

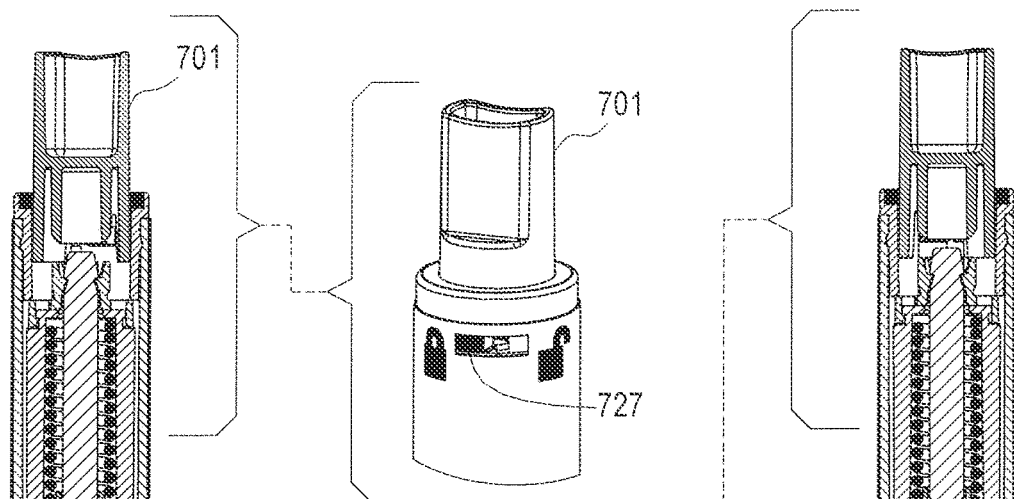
*Fig. 31B*
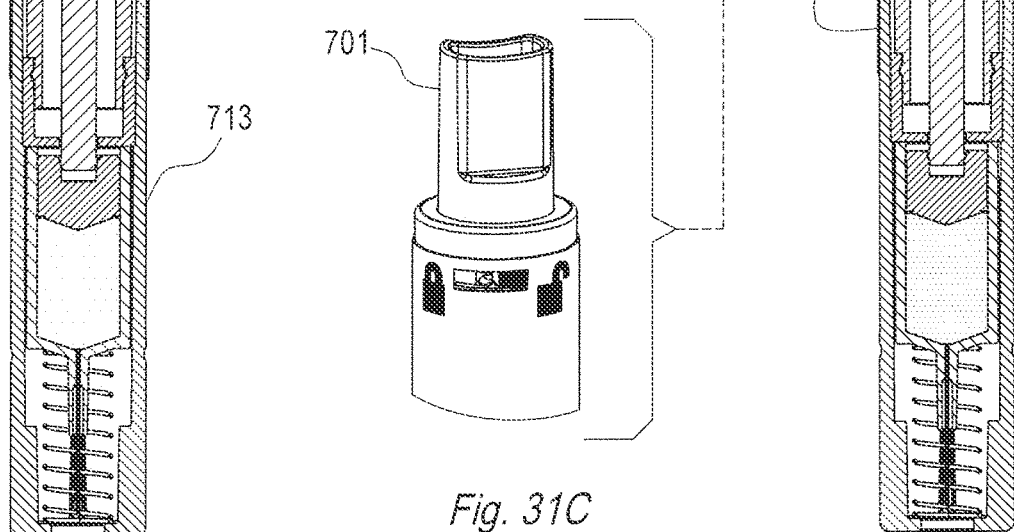
*Fig. 31C*
*Fig. 31A*
*Fig. 31D*

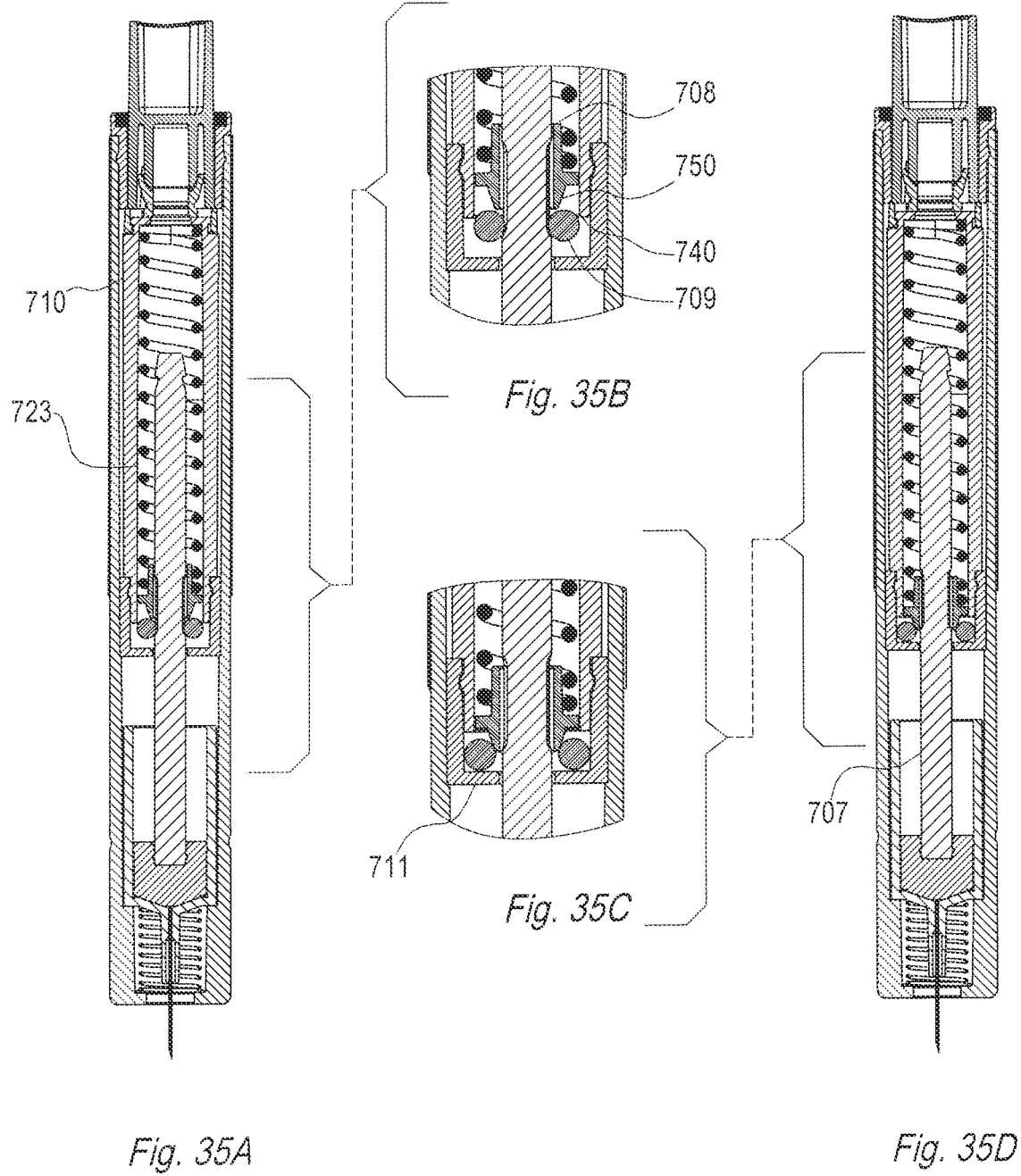

SELF-RETRACTING MECHANIZED SYRINGE AND METHODS OF USE

CROSS-REFERENCE TO RELATED APPLICATIONS

This disclosure is a divisional application of U.S. application Ser. No. 16/158,715, filed Oct. 16, 2018, which claims the benefit of U.S. Provisional Application No. 62/572,645, filed Oct. 16, 2017. Each application, publication and patent listed in this paragraph is hereby incorporated herein by reference in its entirety.

BACKGROUND

Technical Field

The present disclosure is related to an automatic injection and retraction syringe. More particularly, the disclosure is related to a manually operable mechanism which upon actuation by the user inserts a hypodermic needle into living tissue, injects a liquid therapeutic substance and immediately thereafter permanently retracts the hypodermic needle within the device so as to render the hypodermic needle inaccessible.

Background

Communicable blood-borne diseases such as HIV, hepatitis, and others, exist within the general population. The serious health threat posed by exposure to these diseases has increased the desire to prevent inadvertent needle sticks after the administration of injectable substances. Indeed, the desire to avert the transmission of blood-borne diseases brought about through exposure to contaminated hypodermic needles has prompted legislation mandating the provision of means by which the risk of such exposure is mitigated. Many prior art injection devices include various strategies to mitigate the risk of inadvertent needle stick injuries and the transmission of pathogens.

In addition to the foregoing, there is a growing trend to afford patients that must receive injections as part of a medical therapy the means whereby they may self-medicate. Automatic self-injection devices have become increasingly commonplace. They are widely recognized as a valuable means to enable medically untrained users to administer injections while avoiding the emotional trauma associated with the use of conventional syringes. It has been proven that providing injectable substances in self-injection devices increases patient compliance with their prescribed therapy and thereby improves medical outcomes. Among the various strategies for mitigating the risk of needle stick injury and providing the patient a preferred alternative for self-injection, a number of automatic injection devices incorporate self-retracting hypodermic needles.

Thus for the reasons cited above, among others, there remains a present and increasing need for improved automatic self-injection technology.

SUMMARY

An injection and retraction syringe comprises an injection assembly and a drug-Tillable retraction assembly securable to the injection assembly; the injection assembly comprising a housing, a plunger rod, a power means, a latch, an unlatching means, a spring rest, and a coupler operable to engage and disengage from the plunger rod. In the injection and retraction syringe described, the power means, preferably comprising a spring, resides internal to the housing and in contact with the spring rest; the spring rest resides in contact with coupler; coupler remains engaged with the plunger rod so long as the coupler remains in contact with the housing. Further, in the injection and retraction syringe described, a fluid containment means is provided comprising at least one dynamic seal, a fluid containment chamber and a hypodermic needle which is permanently attached to the fluid containment chamber. The plunger rod is configured to impinge upon the dynamic seal upon actuation of the syringe and transfer force thereto. A sealable compartment is provided which houses the hypodermic needle and a return spring; the return spring resides in a partially biased condition and abuts the fluid containment chamber. The dynamic seal is operable to contain a fluid within the fluid containment chamber and displace the fluid out of the chamber through the hypodermic needle. A removable cover is provided and disposed about the end of the syringe that houses the hypodermic needle. The removable cover cooperates in a slide able and sealed engagement with the hypodermic needle. Further, the removable cover provides a connectable and sealable fitting preferably in the form of a tapered socket configured to receive a means to convey fluid through the cover, through the hypodermic needle and into the fluid containment chamber. Preferably, a means to close the connectable fitting disposed on the cover may be provided. In the injection and retraction syringe described, the sealed volume and fluid path may preferably be sterile. An alternative embodiment provides a sub-assembly comprising a medicament container, a hypodermic needle, and a single dynamic seal. The medicament container is disposed internal to a housing and configured move axially within the housing in a sliding relationship within the interior of the housing. In this embodiment, the dynamic seal is configured to travel axially in a slide able relationship within the interior of the medicament container. A hypodermic needle is permanently affixed at the distal end of the syringe body medicament container and provides a conduit through which fluid may pass into and/or out of the medicament container. A retraction spring is disposed distal to and in contact on the return spring's proximal end with the exterior distal surface of the medicament container. The return spring is also in contact on its distal end with the interior, proximally-disposed surface of the housing whereupon the return spring is retained axially in a partially biased condition. In its ready-to-use state, the medicament container is urged in the proximal direction by the partially biased return spring and causes the medicament container to rest upon a distally disposed interior surface.

There is disclosed further a plurality of methods of producing a ready-to-use combination of medicinal fluid and a mechanism for automatically injecting the medicinal fluid into living tissue. In the methods described, the mechanism being prepared could be the self-retracting mechanized syringe describe above, although the methods disclosed are not limited to use of a particular syringe. In one method described, the medicinal fluid is filled into the fluid containment chamber of the present invention by affixing a fluid transfer device to the connectable and sealable fitting disposed on the cover and transporting the fluid from the fluid transfer device proximally into the fluid containment chamber through the hypodermic needle provided by the present invention.

DRAWINGS

Non-limiting embodiments of the present disclosure are described by way of example in the following drawings, which are schematic and are not intended to be drawn to scale:

FIGS. 7A through 7F show further details of the upper region of upper subassembly of FIGS. 2 and 4 in cross section.

FIGS. 8A through 8C are section views taken along the long axis and describe an alternative embodiment of the upper subassembly.

FIGS. 10A through 10C show further details of the upper and lower regions of the lower subassembly of FIGS. 3 and 5.

FIGS. 12 through 19 provide cross sectional views of a first embodiment of the automatic injection and retraction syringe during notable states and various transitional states during usage sequence.

Figure 12:
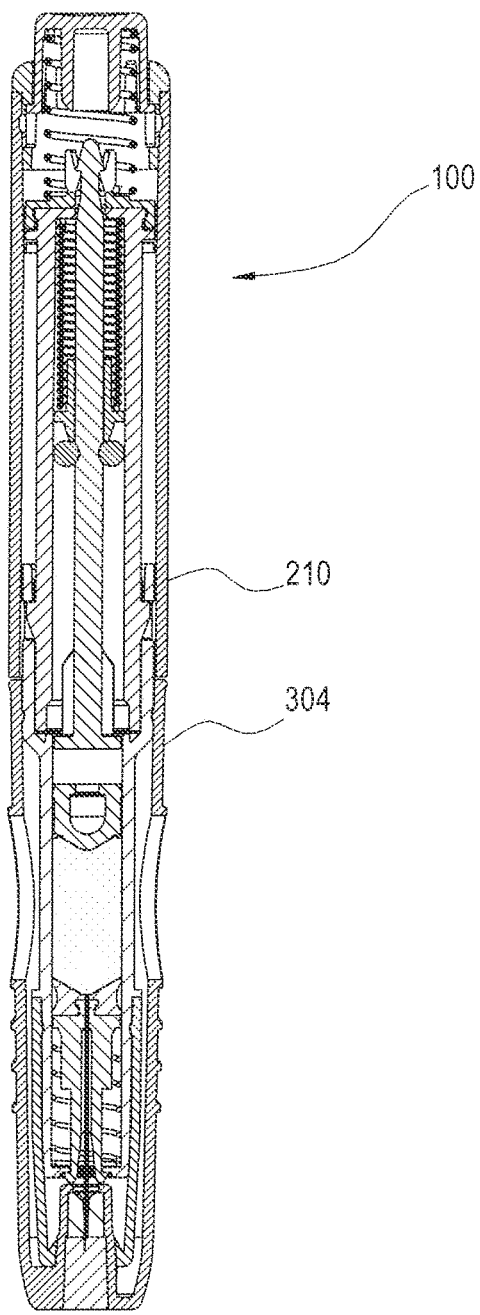

FIG. 12 illustrates the automatic injection and retraction syringe in a ready-to-use state whereupon it is filled with medicament and provided to the user.

Figures 13A, 13B:
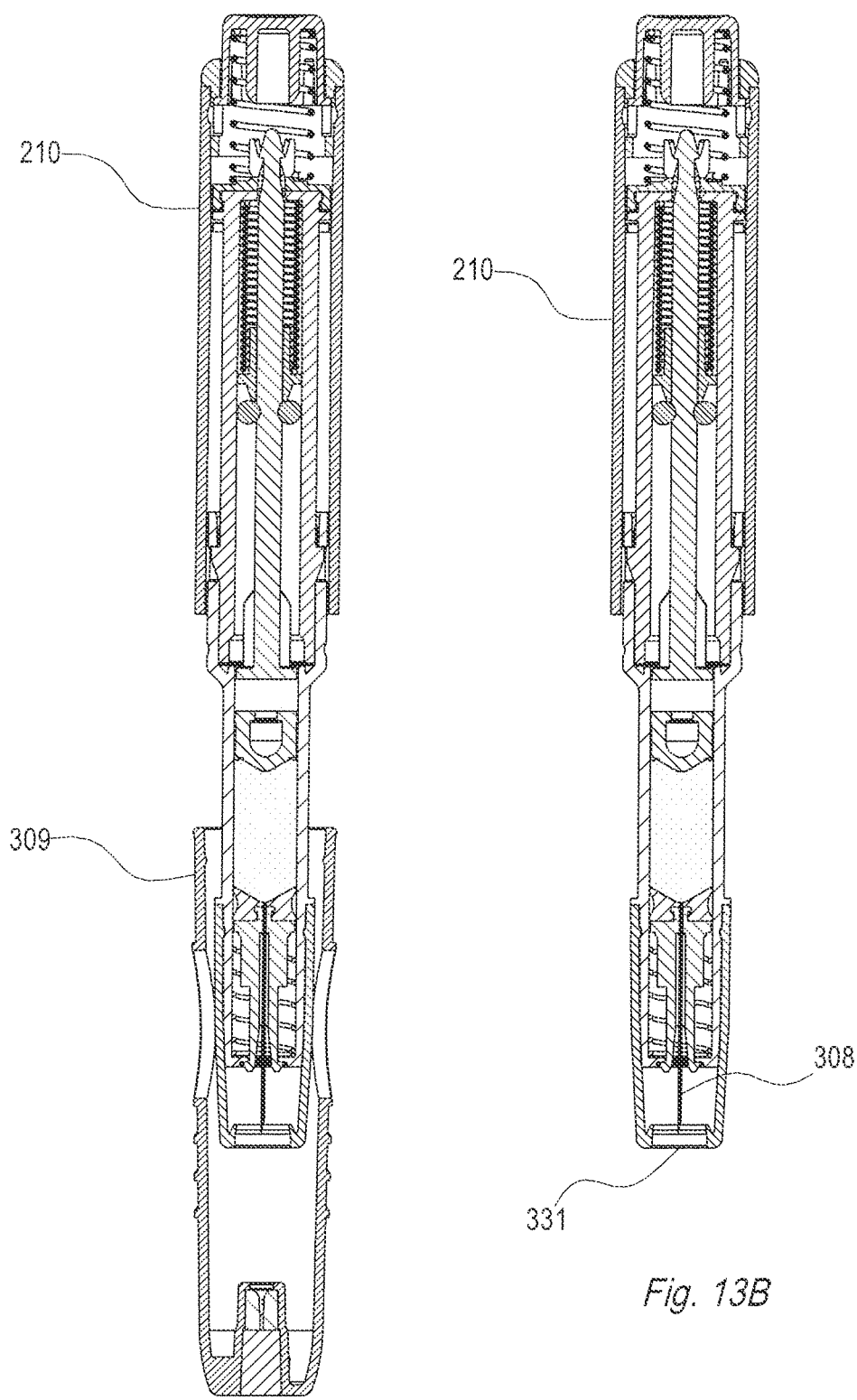

FIGS. 13A and 13B illustrate the automatic injection and retraction syringe during and after cap removal.

Figure 14A:
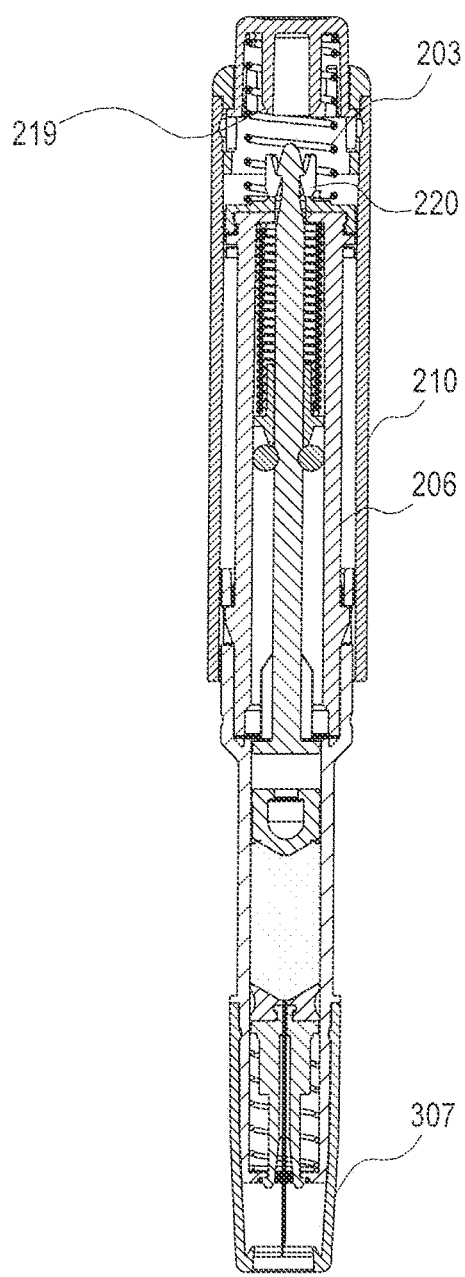
Figure 14B:
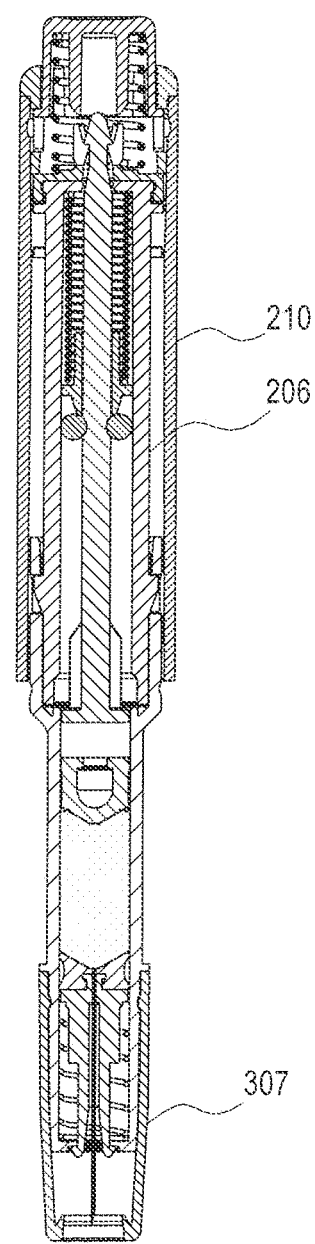

FIGS. 14A and 14B illustrate the automatic injection and retraction syringe transitioning into state of activation prior to actuation.

Figures 15A, 15B:
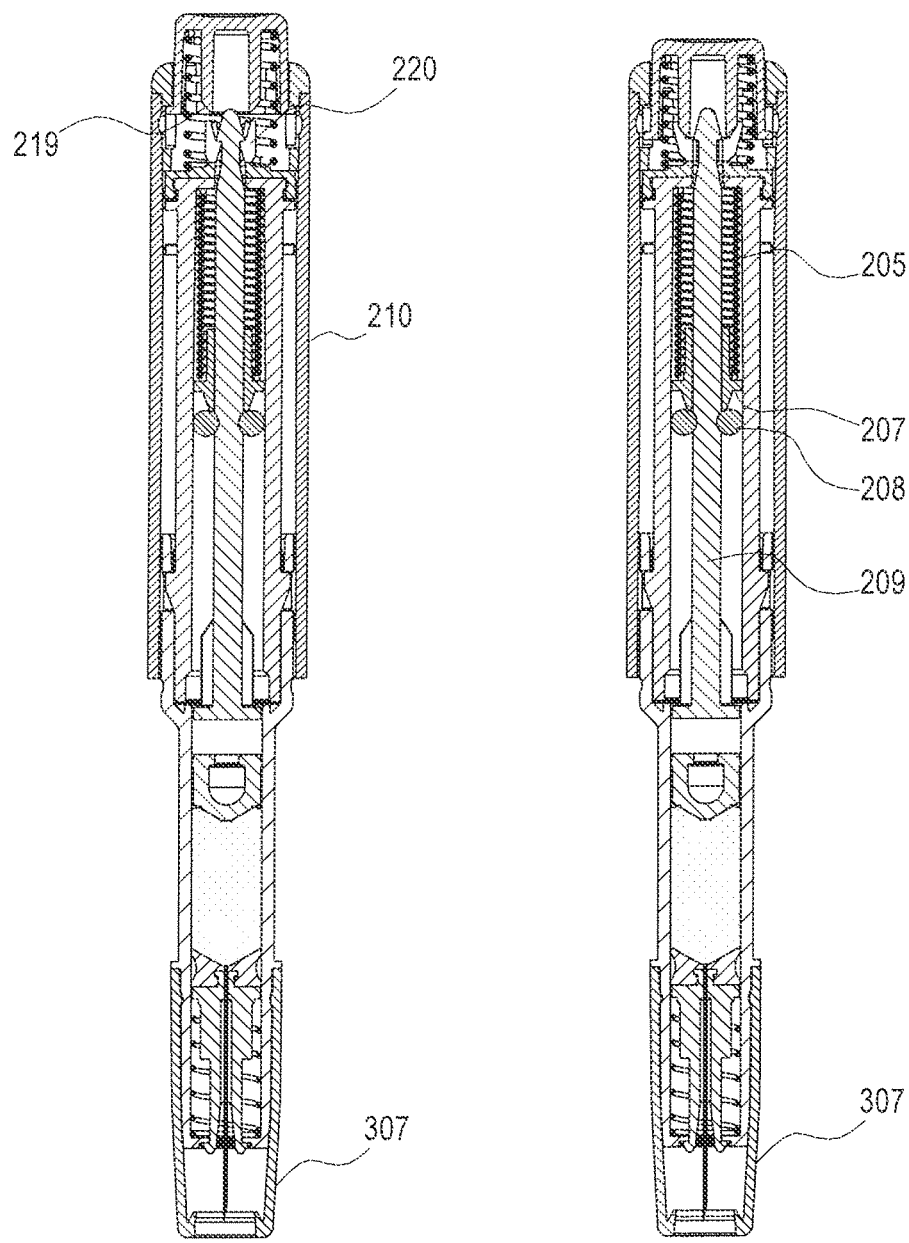

FIGS. 15A and 15B illustrate the automatic injection and retraction syringe while activated and transitioning into state of actuation prior to plunger rod travel.

Figures 16A, 16B:
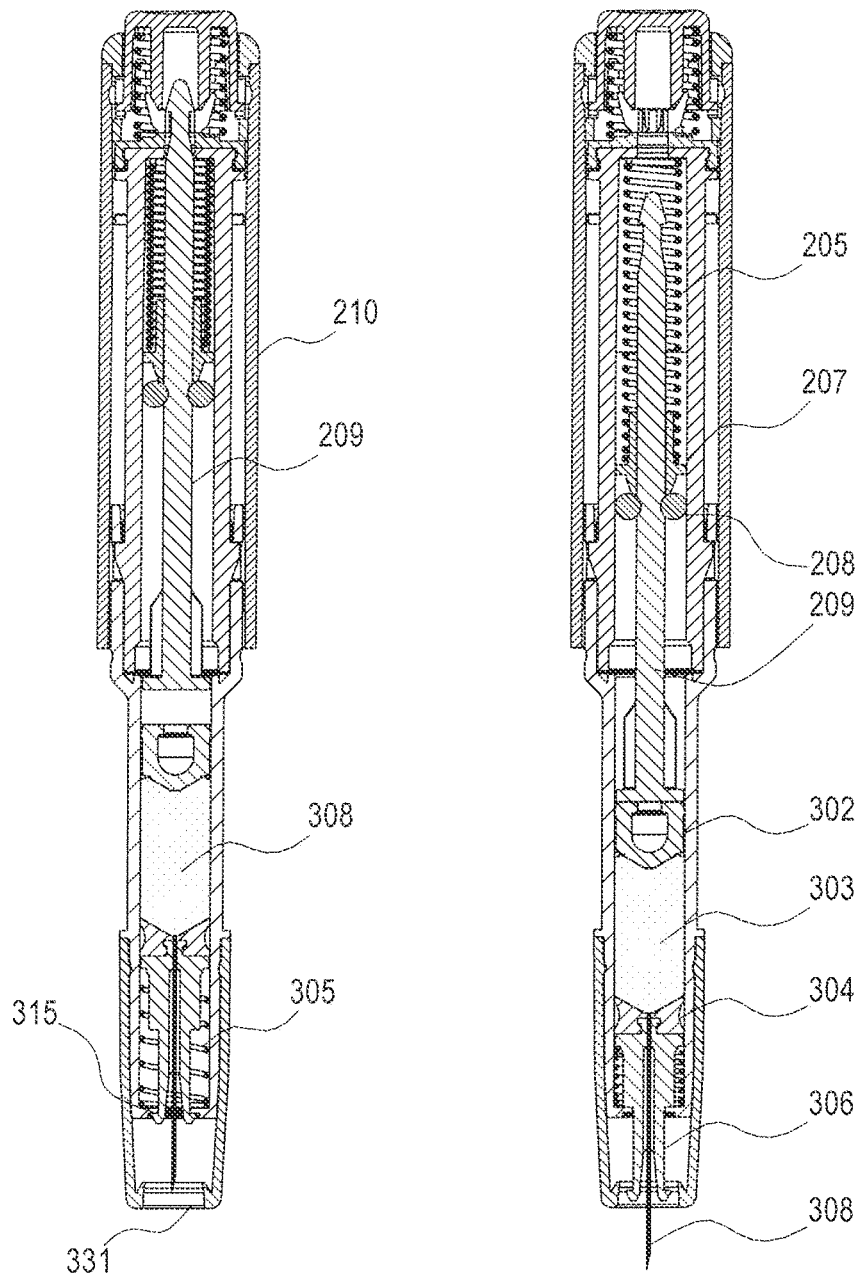

FIGS. 16A and 16B illustrate the automatic injection and retraction syringe transitioning into state of full hypodermic needle extension and prior to dose delivery.

Figure 17A:
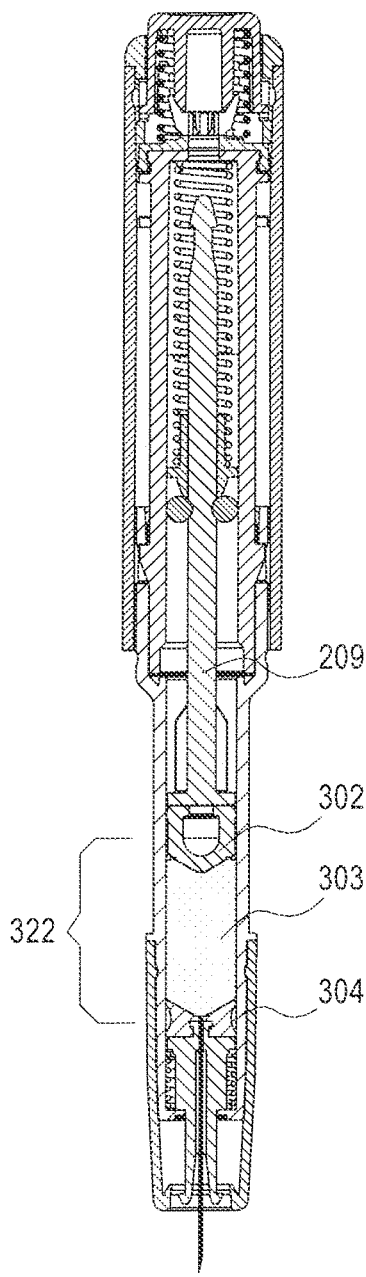
Figure 17B:
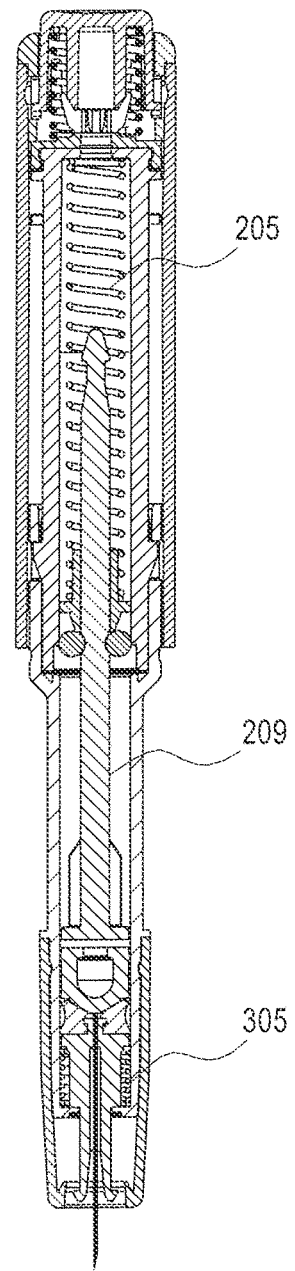

FIGS. 17A and 17B illustrate the automatic injection and retraction syringe transitioning into state of full dose delivery prior to release of plunger rod.

FIGS. 18A through 18D illustrate the automatic injection and retraction syringe transitioning into state of plunger rod release just prior to needle retraction.

Figure 19A:
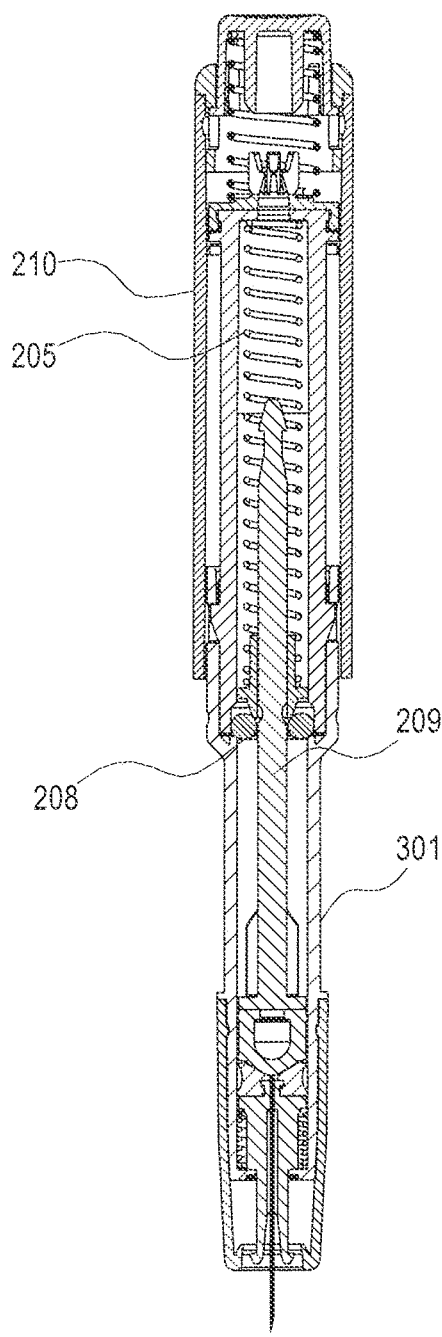
Figure 19B:
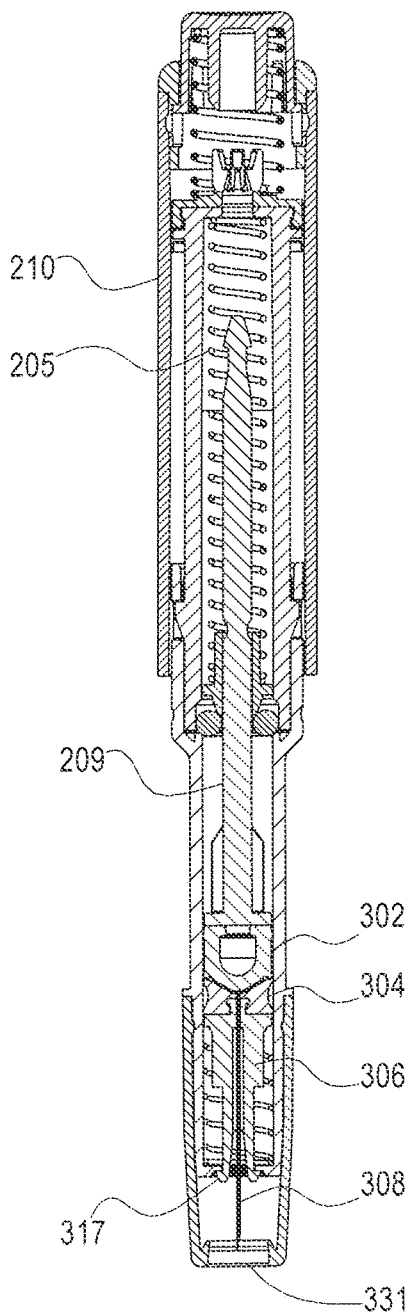

FIGS. 19A and 19B illustrate automatic injection and retraction syringe transitioning into state of needle retraction.

Figure 2:
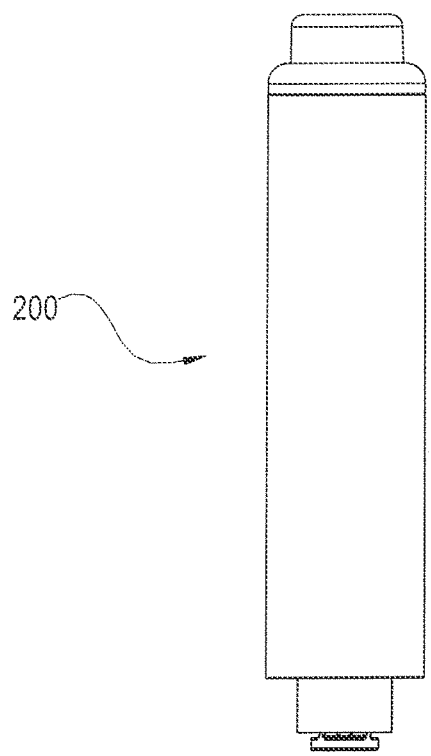
FIGS. 2 and 3 are exterior front elevation views of the two major subassemblies of an embodiment of the self-retracting mechanized syringe according to the present disclosure prior to final assembly.
Figure 4A:
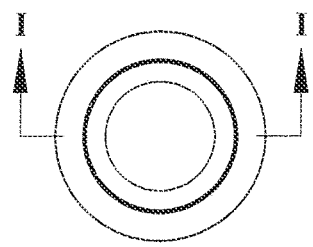
FIGS. 4A and 4B show a cross section of the upper subassembly illustrated in FIG. 2 with the section taken along the long axis.
Figure 4B:
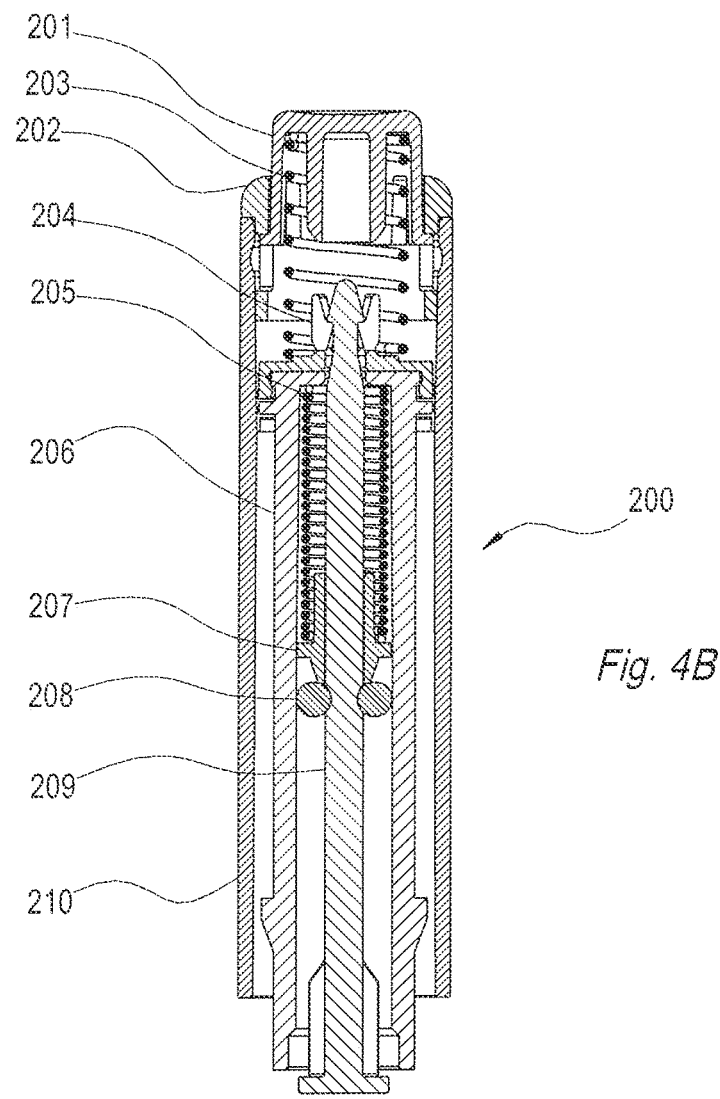
Figure 20:
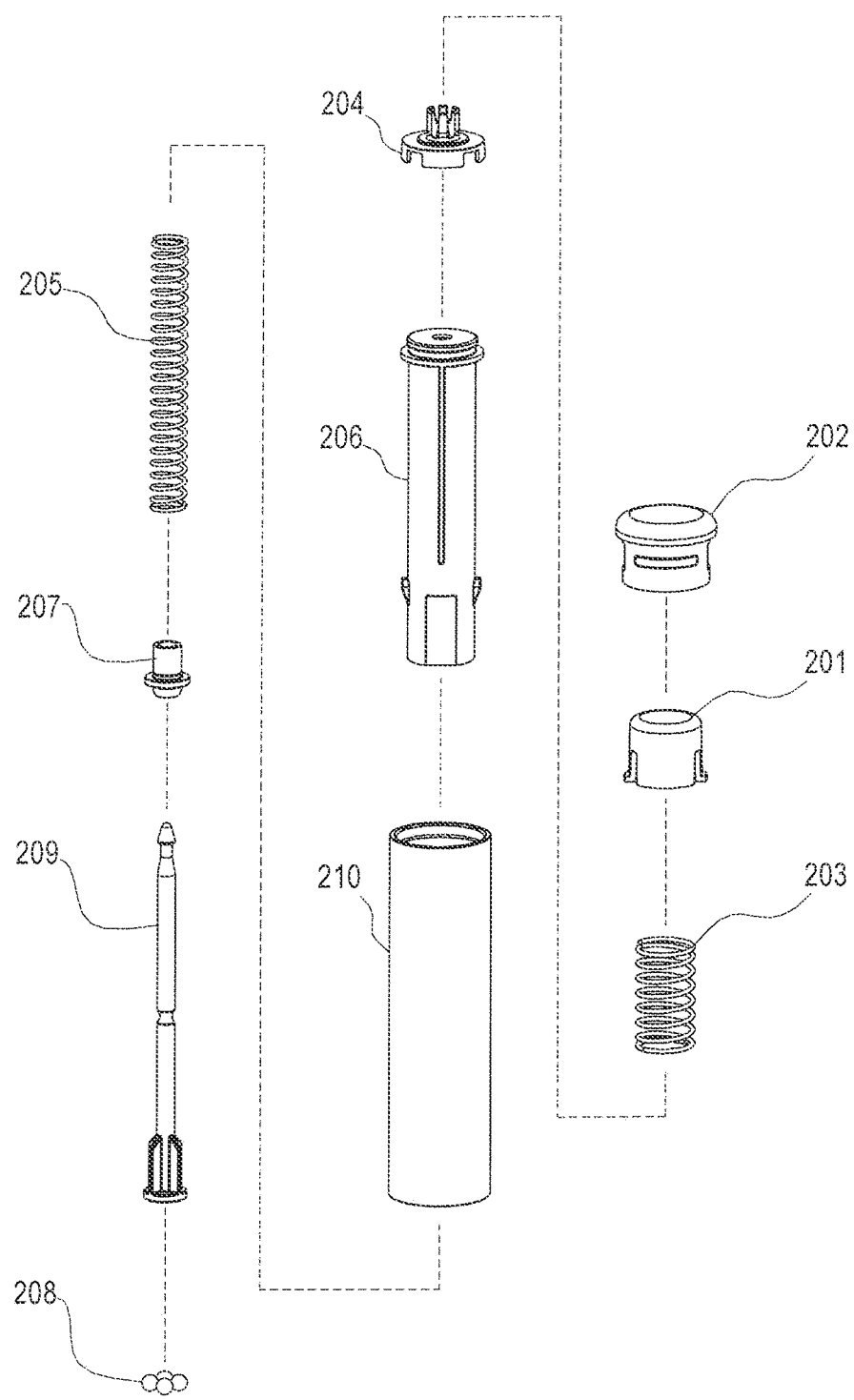

FIG. 20 is an exploded view of the upper subassembly of FIGS. 2 and 4.

Figure 3:
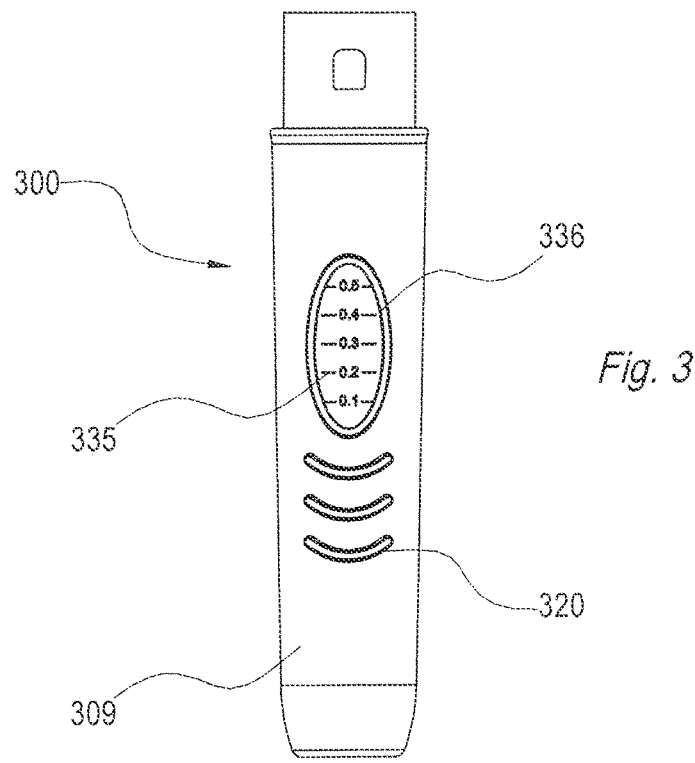
Figure 5A:
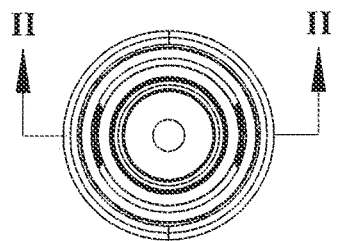
FIGS. 5A and 5B show a cross section of the lower subassembly shown in FIG. 3 with the section taken along the long axis and in the same plane as FIG. 4.
Figure 5B:
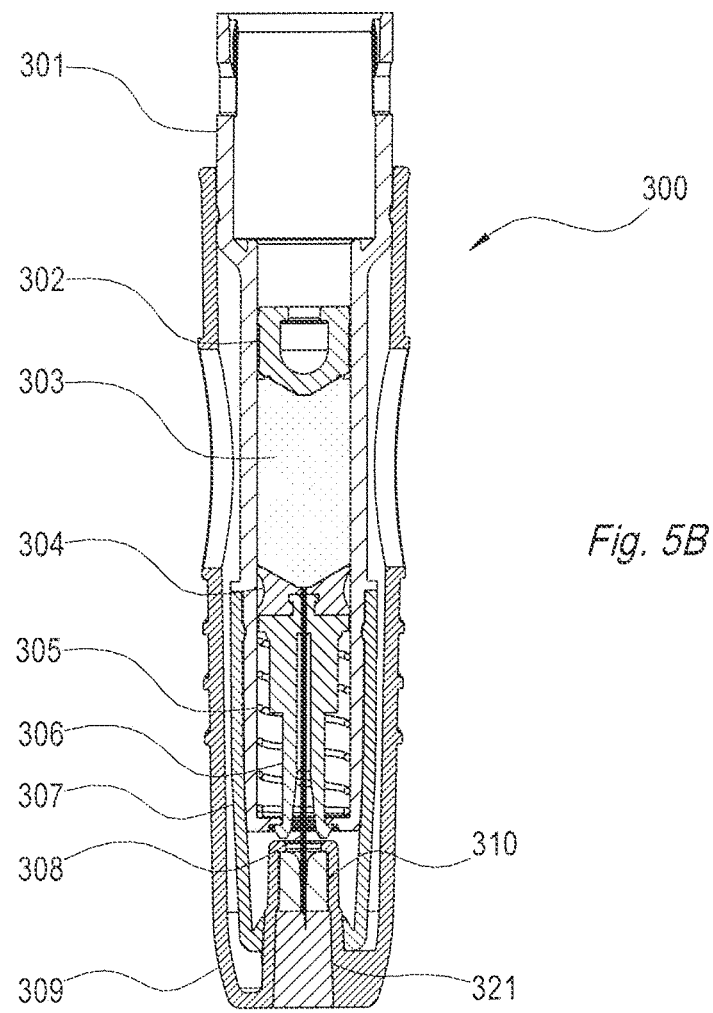
Figure 21:
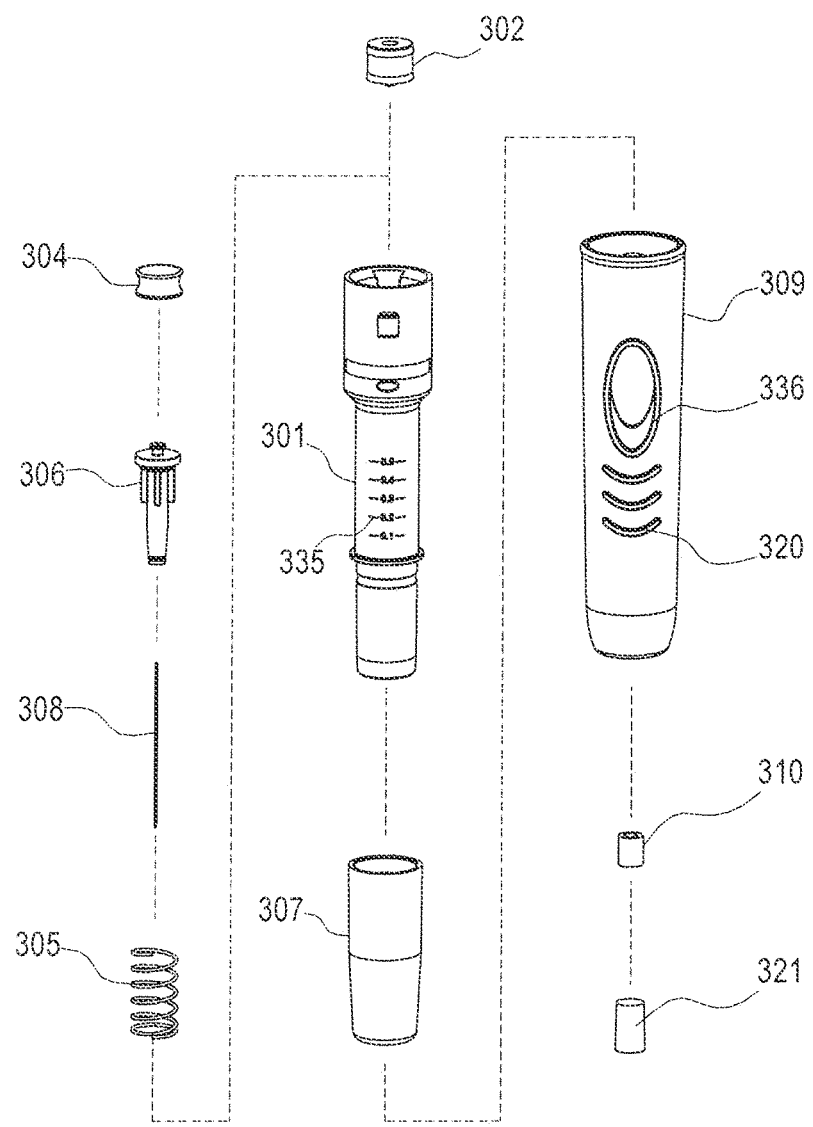

FIG. 21 is an exploded view of the lower subassembly of FIGS. 3 and 5.

FIGS. 22A through 22E illustrate a method for filling the medicament into the automatic injection and retraction syringe.

Figures 23A, 23B, 23C:
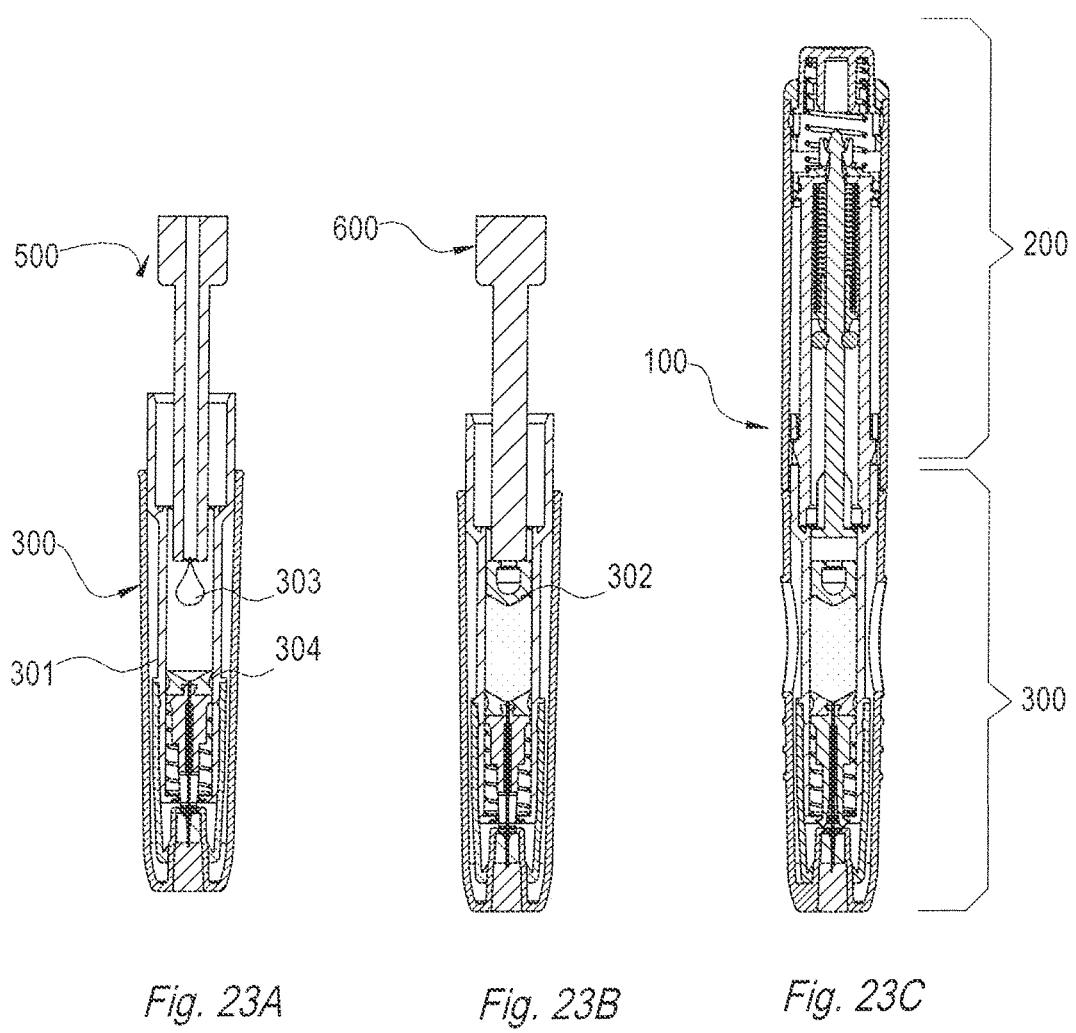

FIGS. 23A through 23C illustrate a method for filling the medicament into the lower subassembly and completing final assembly of the syringe.

Figure 24:
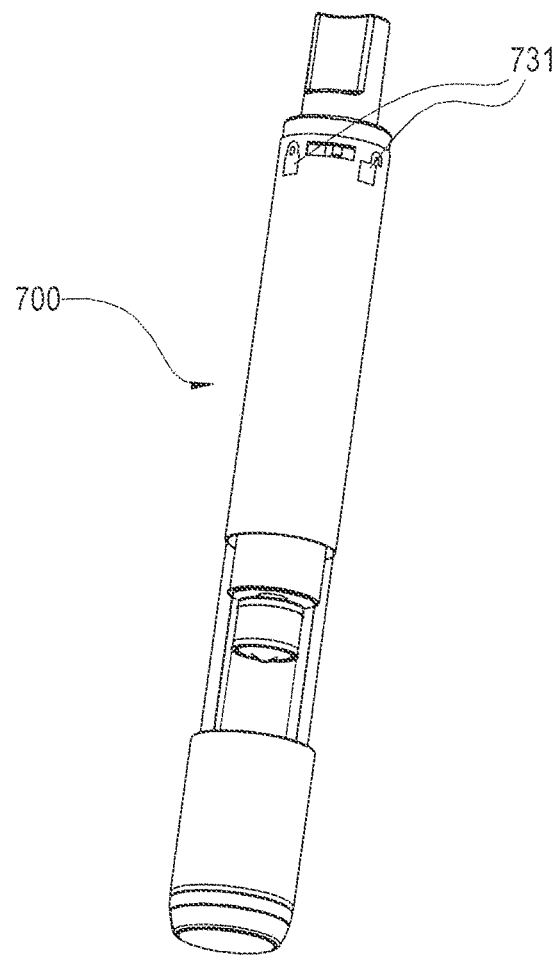

FIG. 24 illustrates the front elevation of a second embodiment of the present invention.

Figure 25A:
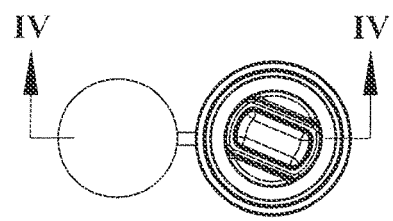
Figure 25B:
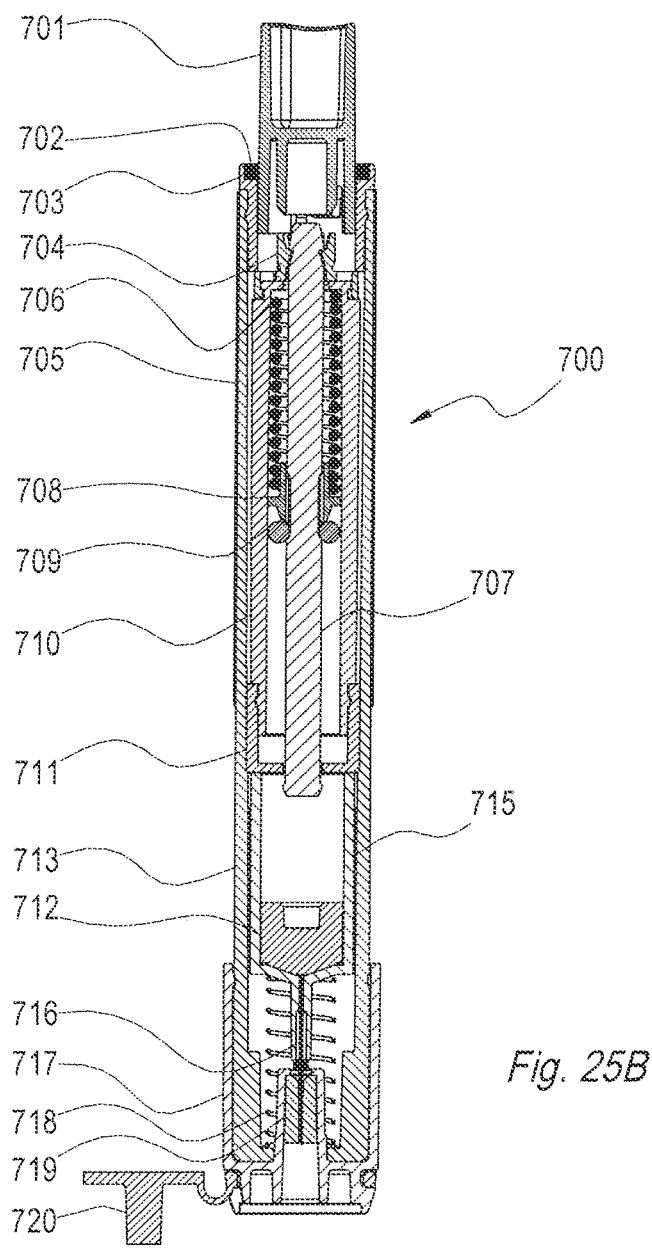

FIGS. 25A and 25B illustrate a cross section of a second embodiment of the present invention with the section taken at the center axis.

Figures 26A, 26B:
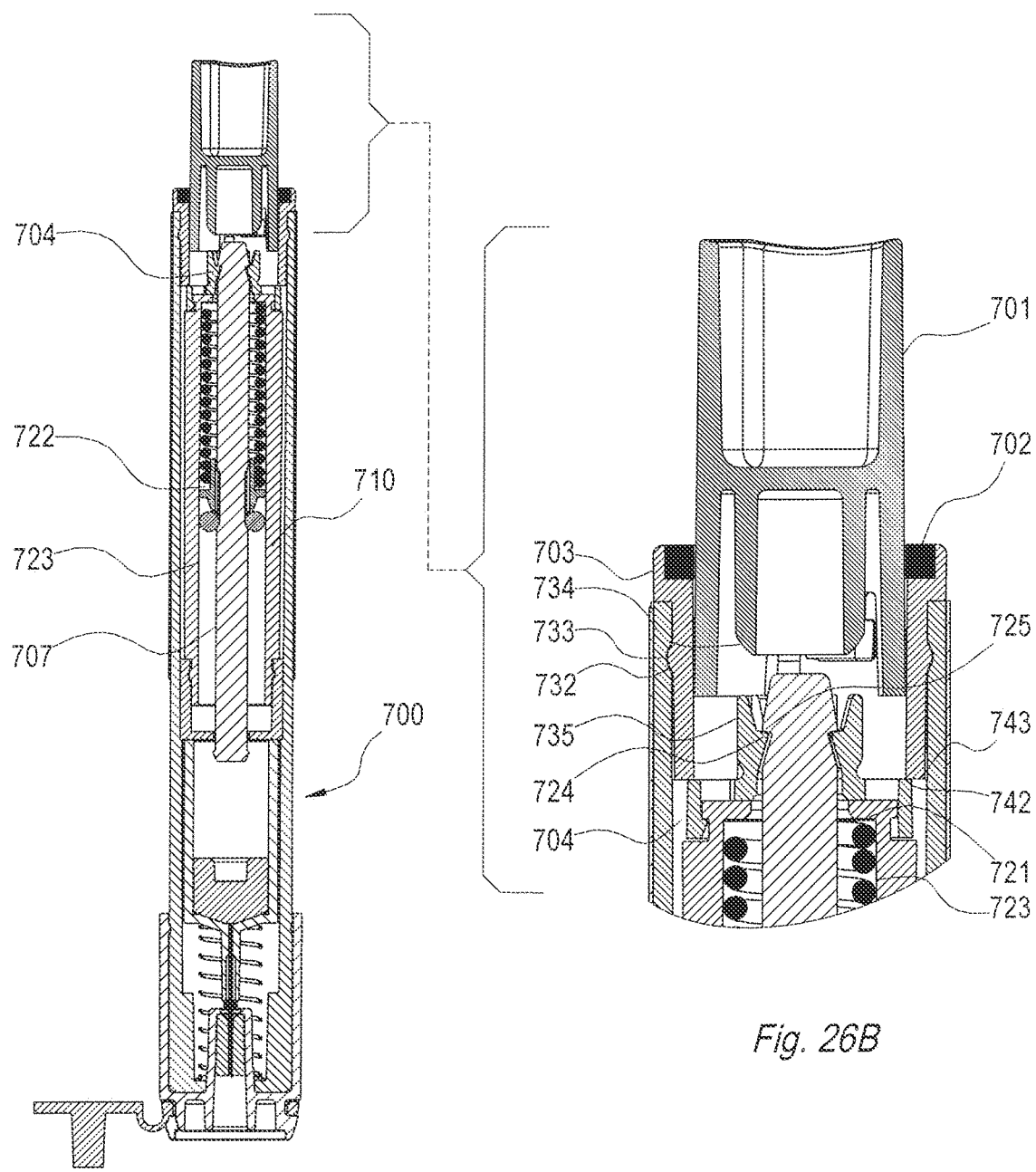

FIGS. 26A and 26B illustrate a cross section of a second embodiment of the present invention and provides additional detail of the proximal end.

Figure 27A:
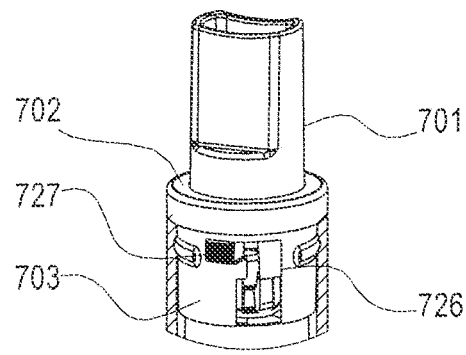
Figure 27B:
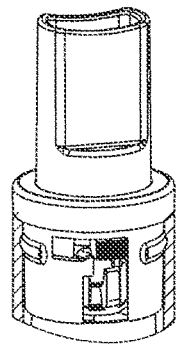
Figure 27C:
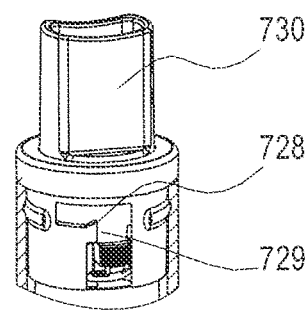

FIGS. 27A through 27C illustrate a partial cross section of the proximal end of a second embodiment of the present invention and provide further detail of a rotating locking/unlocking actuation button.

Figures 28A, 28B:
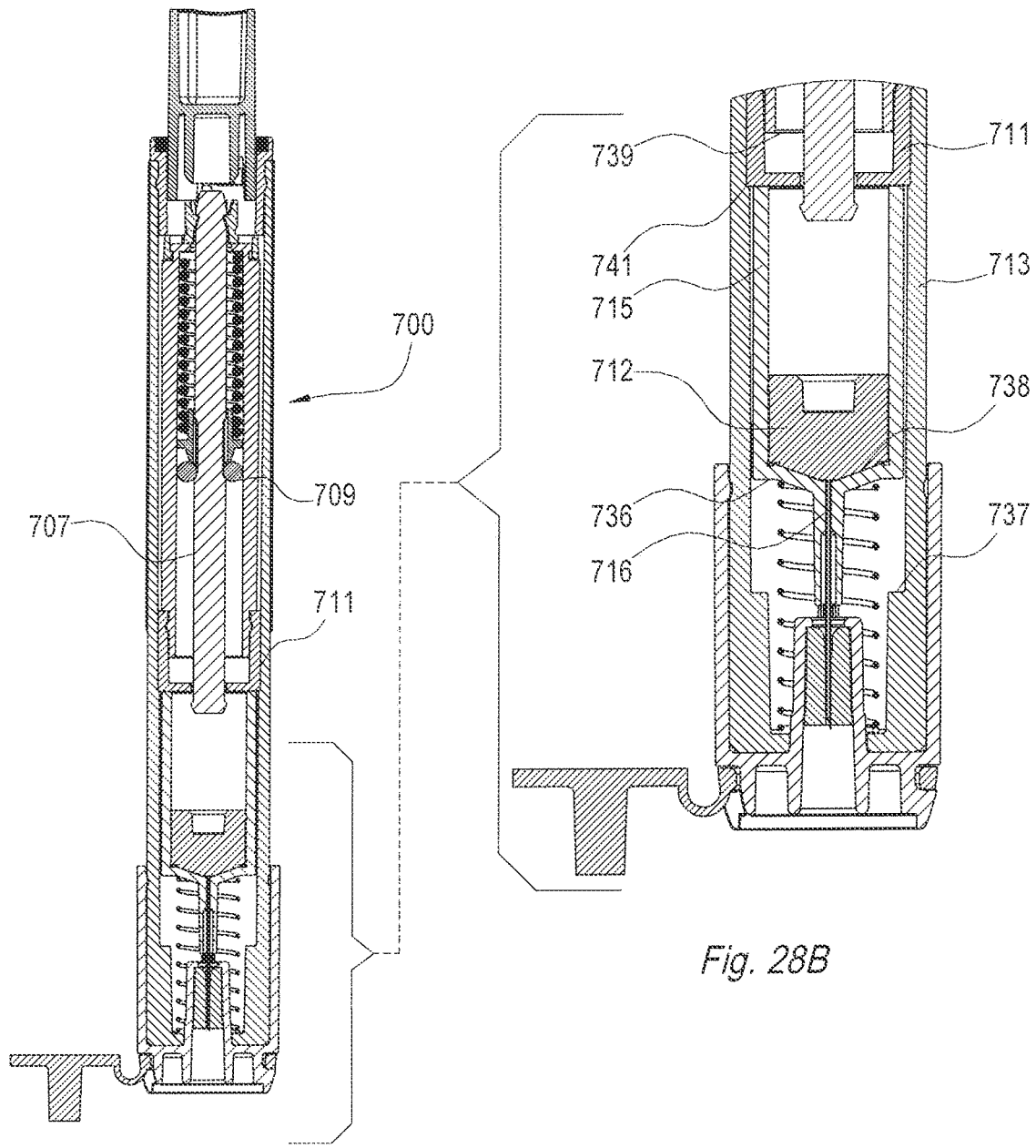

FIGS. 28A and 28B illustrate a cross section of a second embodiment of the present invention and provides additional detail of the distal end.

Figures 29A, 29B, 29C:
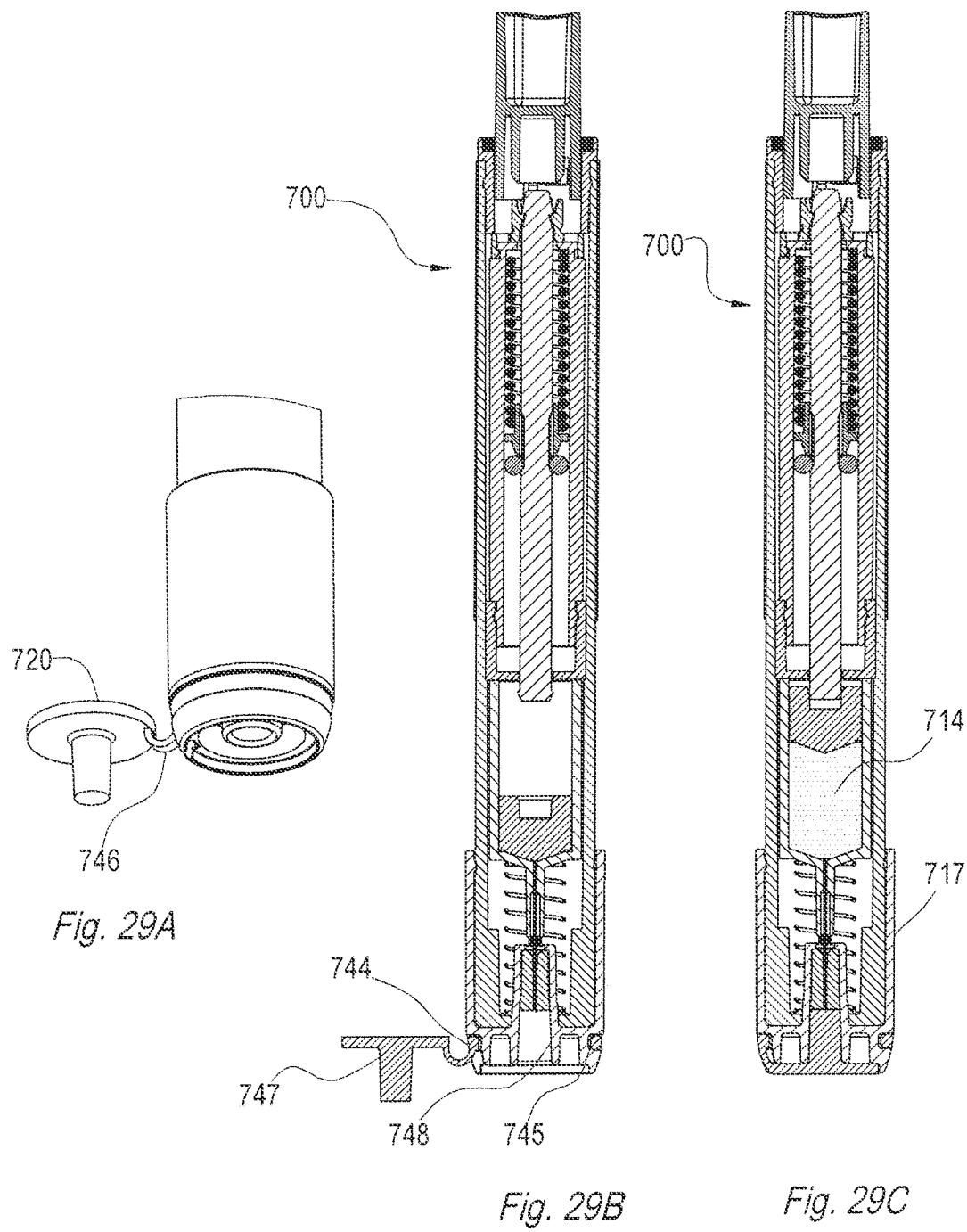

FIGS. 29A through 29C illustrates a cross section of a second embodiment of the present invention and further illustrates the operation of an attached plug configured to seal the distal end of removable cap.

FIGS. 30 through 35 provide cross sectional and pictorial views of a second embodiment of the present invention during notable states and illustrate various transitional states during the usage sequence.

Figures 30A, 30B, 30C:
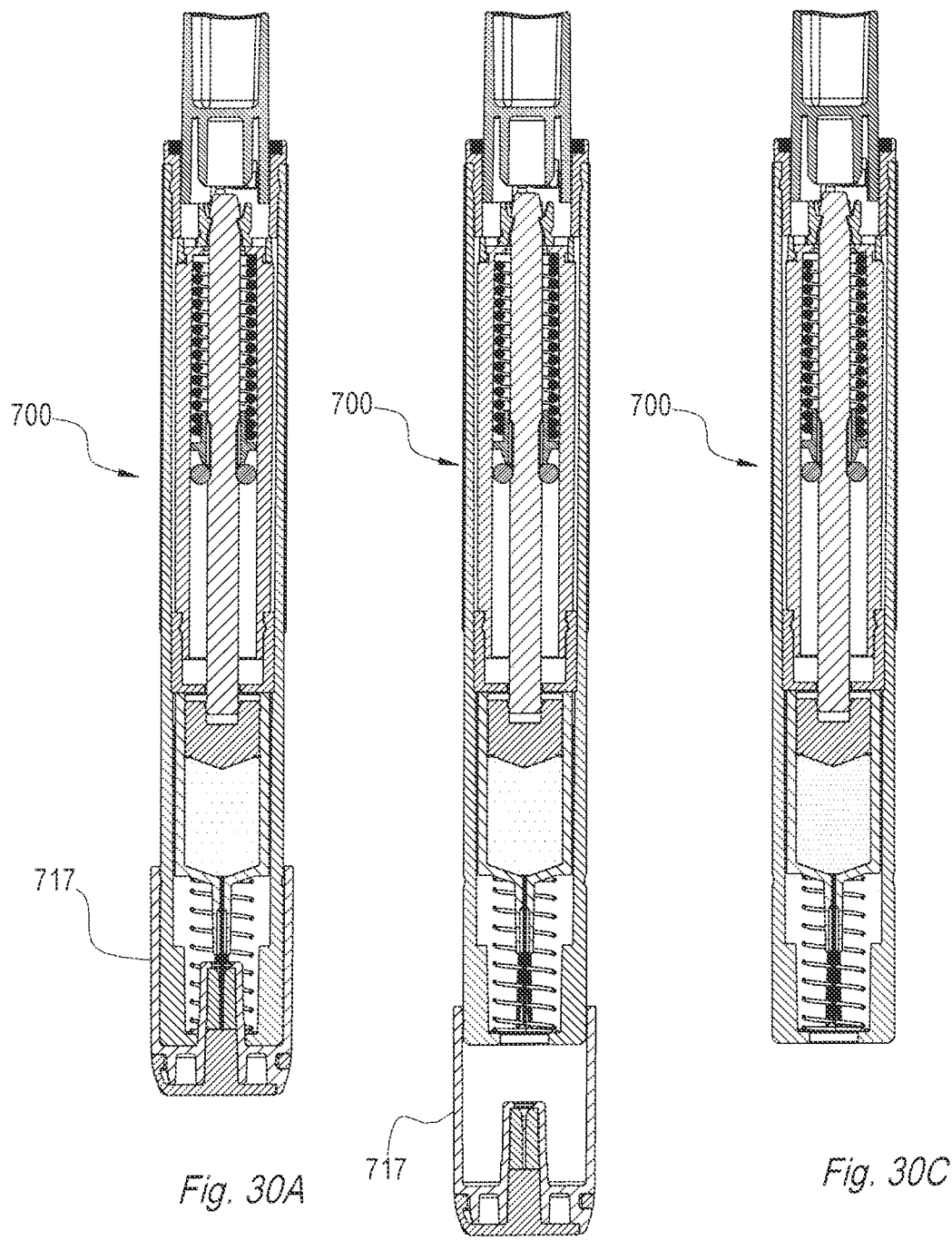

FIGS. 30A through 30C illustrate a second embodiment of the present invention during and after cap removal.

FIGS. 31A through 31D illustrate a second embodiment of the present invention as the actuation button transitions from an inactivated state to an activated state.

Figures 32A, 32B:
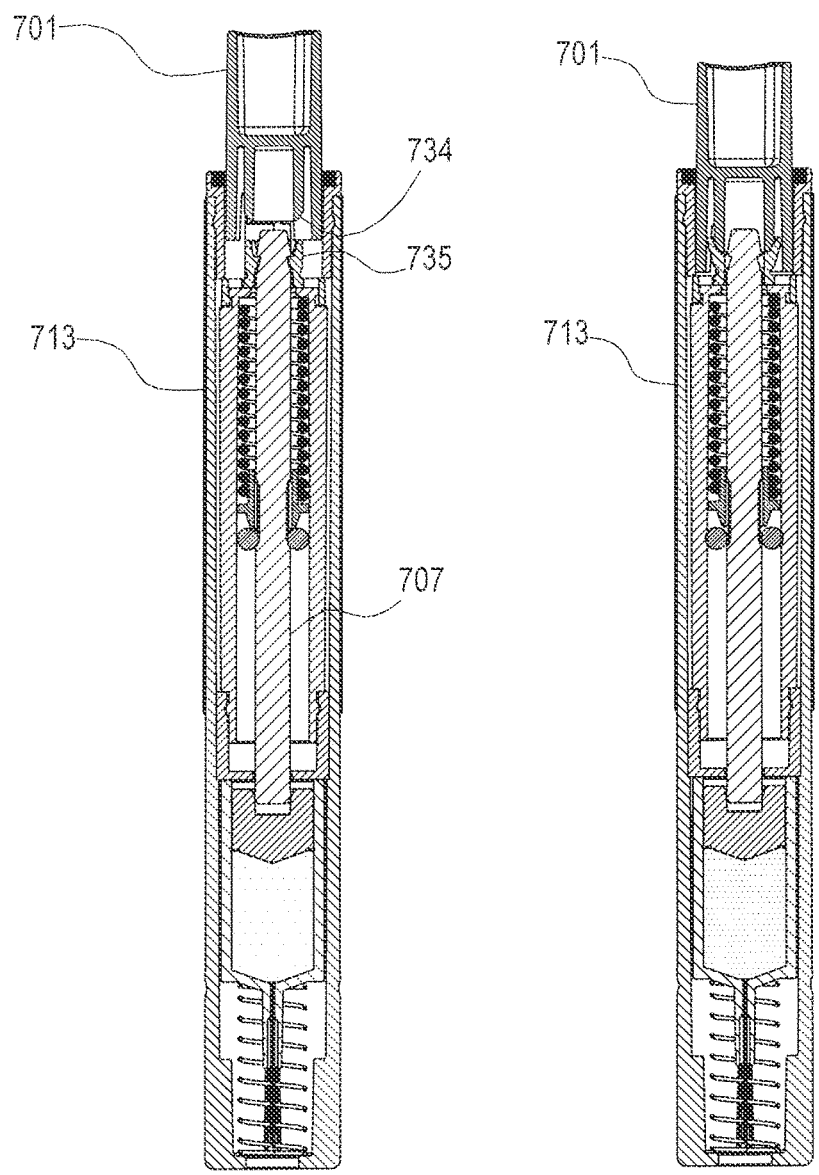

FIGS. 32A and 32B illustrate a second embodiment of the present invention as the activated button is actuated.

Figures 33A, 33B:
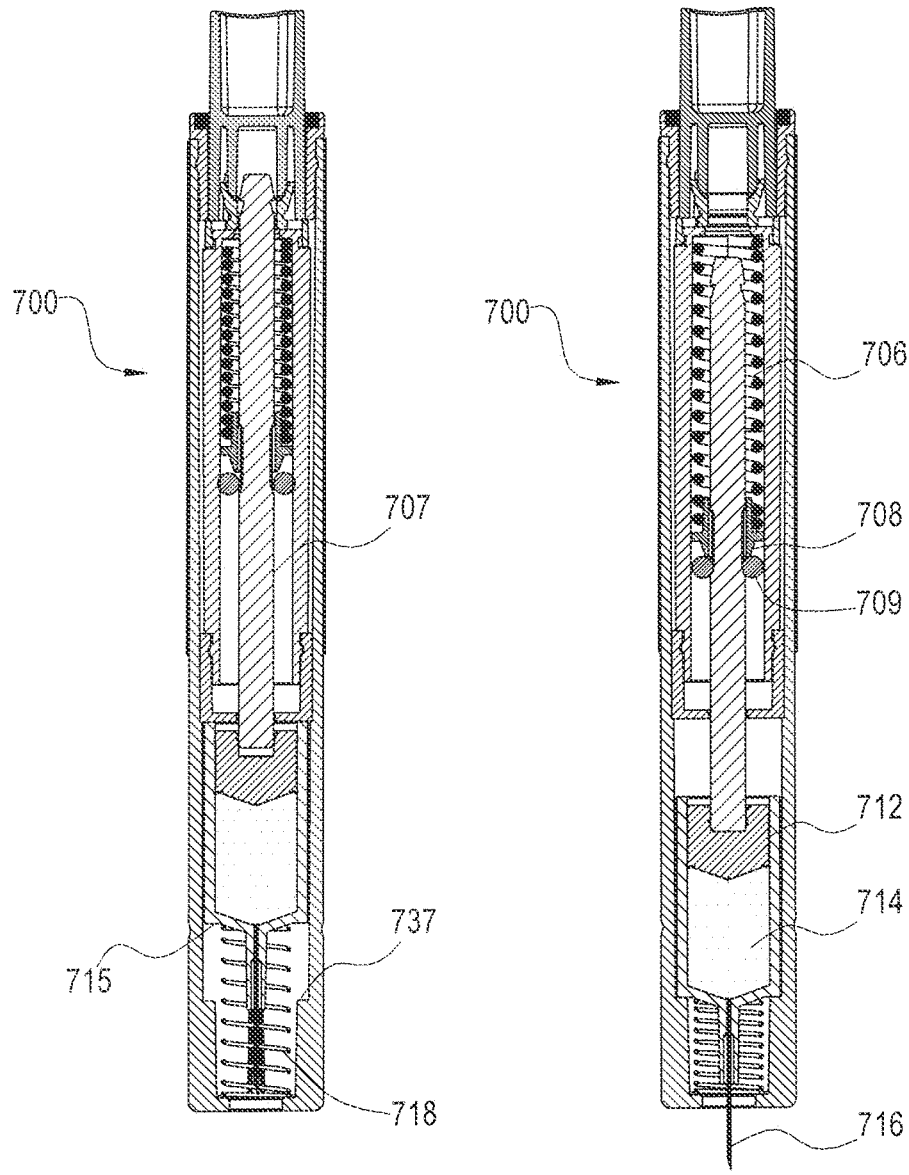

FIGS. 33A and 33B illustrate a second embodiment of the present invention transitioning into the state of full hypodermic needle extension and prior to dose delivery.

Figures 34A, 34B:
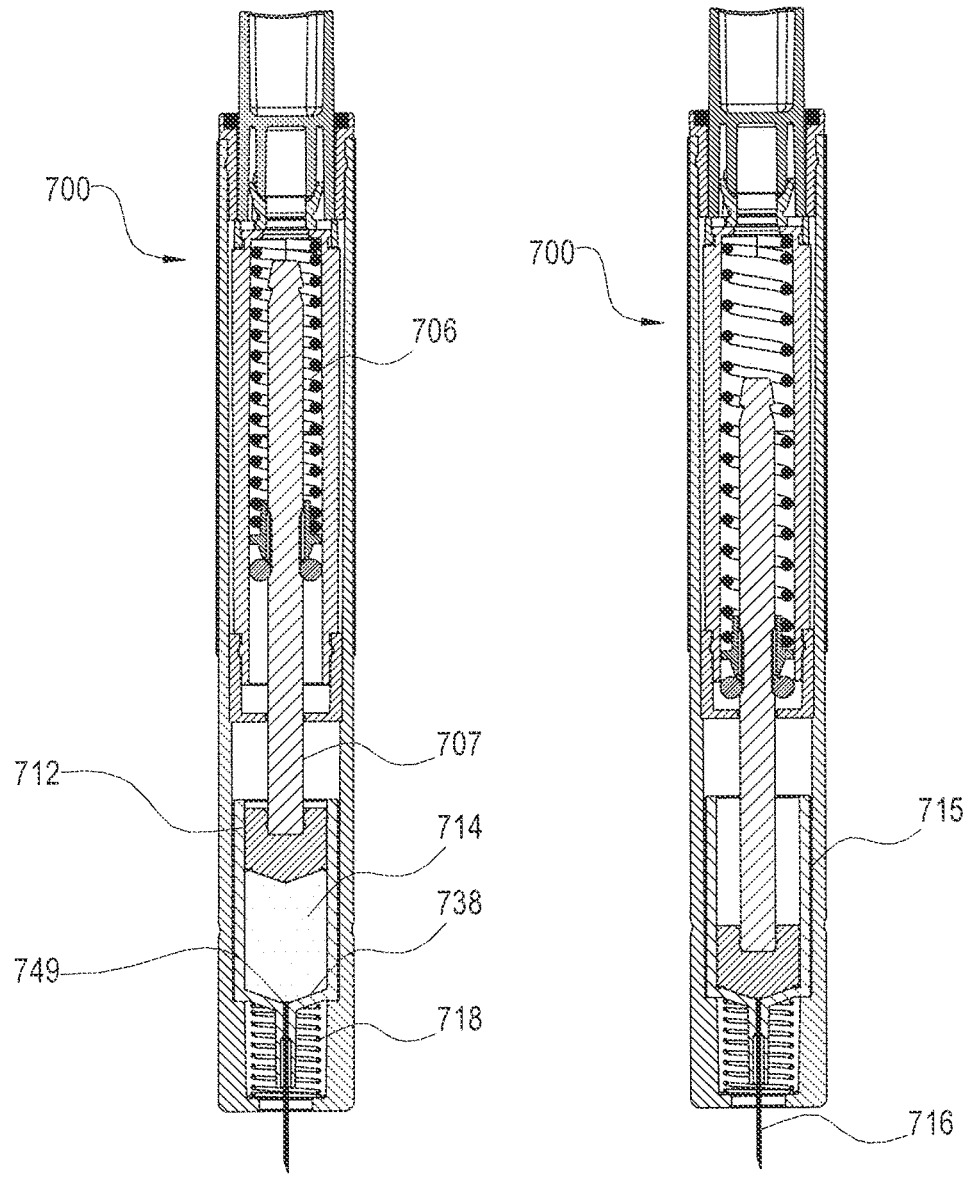

FIGS. 34A and 34B illustrate a second embodiment with the hypodermic needle fully extended and transitioning into the state of full dose delivery.

FIGS. 35A through 35D illustrate a second embodiment in a state of plunger rod release and prior to syringe retraction.

Figures 36A, 36B:
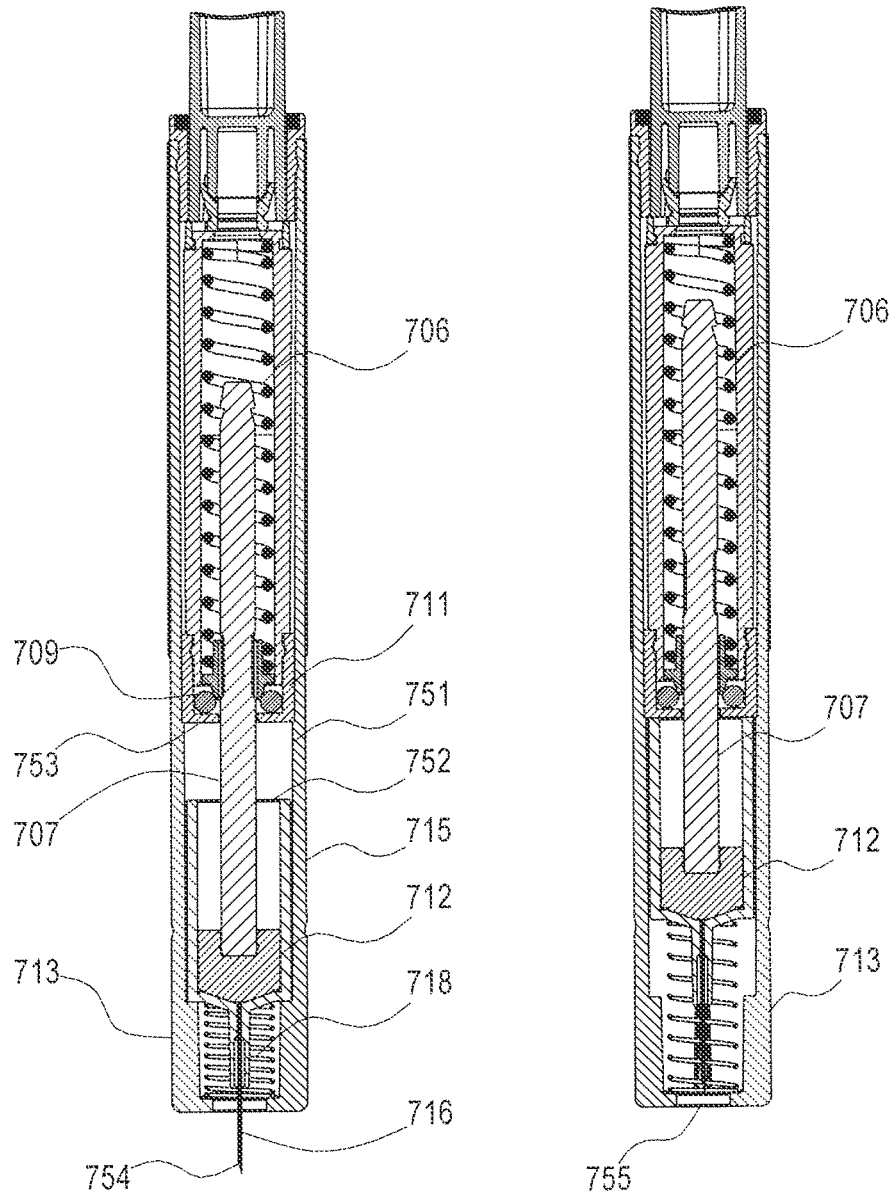

FIGS. 36A and 36B illustrate a second embodiment as the plunger rod and syringe assembly transition to the retracted state.

Figure 37:
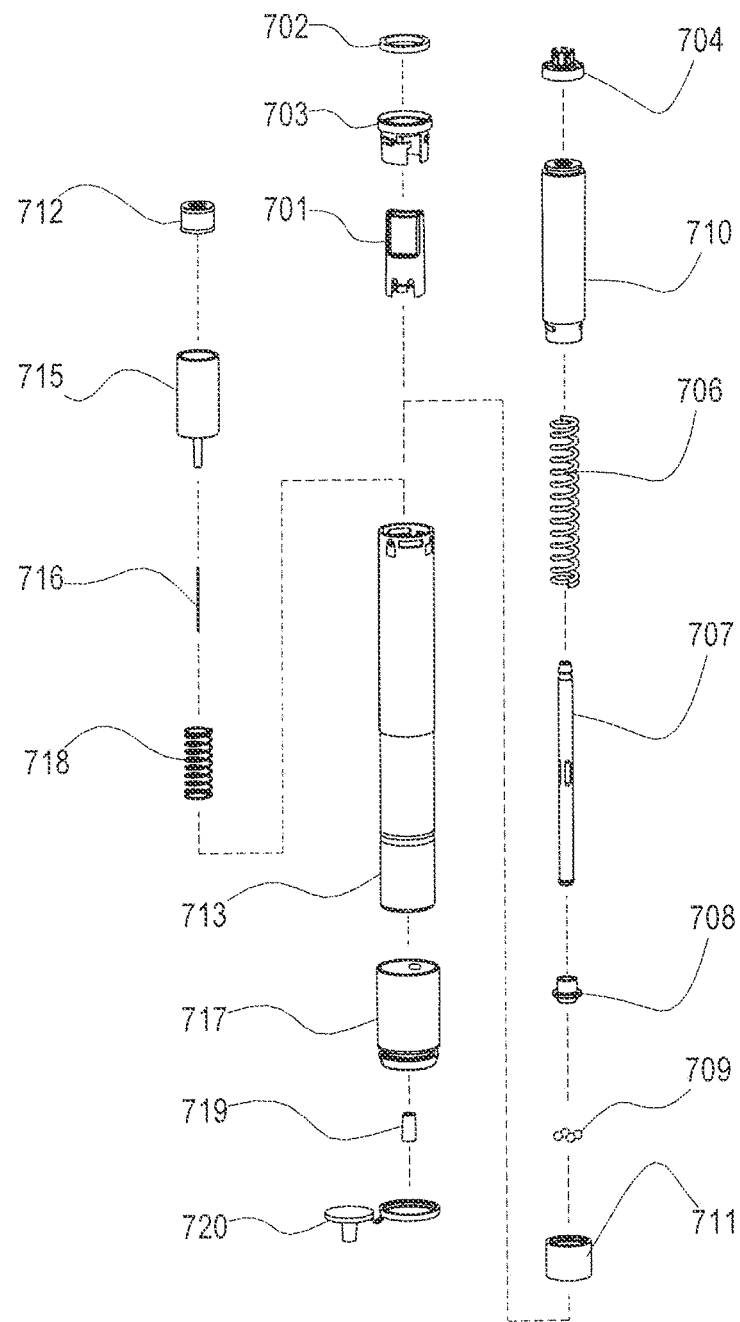

FIG. 37 is an exploded view of a second embodiment of the present invention.

FIGS. 38A through 38E illustrates a method of filling the medicament into a second embodiment of the present invention and sealing the end of the removable cap.

| INDEX OF REFERENCE NUMERALS | |
|---|---|
| Reference | Element |
| 100 | automatic injection and retraction syringe |
| 200 | upper subassembly |
| 201 | button |
| 202 | sleeve cap |
| 203 | button return spring |
| 204 | latch |
| 205 | needle insertion/fluid injection spring |
| 206 | housing |
| 207 | spring rest |

-continued

INDEX OF REFERENCE NUMERALS

| Reference | Element |
|---|---|
| 208 | coupler |
| 209 | plunger rod |
| 210 | sleeve |
| 211 | housing relief |
| 212 | -- not used -- |
| 213 | aperture |
| 214 | latch proximal face |
| 215 | housing annular flange |
| 216 | sleeve retaining feature |
| 217 | sleeve cap shoulder |
| 218 | proximally disposed tip of latch finger |
| 219 | cam |
| 220 | latch finger |
| 221 | latch shoulder |
| 222 | plunger rod shoulder |
| 223 | fulcrum point |
| 224 | alternative sleeve cap |
| 225 | spring rest flange |
| 226 | housing bore |
| 227 | spring rest bore |
| 228 | sleeve cap window |
| 229 | button arm |
| 230 | annular engaging surface |
| 231 | plunger rod groove |
| 232 | plunger rod flange |
| 233 | housing male snap fit feature |
| 234 | housing counterbore |
| 235 | distally disposed surface |
| 236 | male snap fit feature on sleeve cap |
| 237 | female snap fit feature on sleeve |
| 238 | sleeve longitudinal ribs |
| 239 | housing longitudinal rib |
| 240 | -- not used -- |
| 241 | latch snap fit feature |
| 242 | latch snap fit receiver |
| 300 | lower subassembly |
| 301 | syringe body |
| 302 | upper dynamic seal |
| 303 | fluid medicament |
| 304 | lower dynamic seal |
| 305 | needle retraction spring |
| 306 | retainer |
| 307 | nose |
| 308 | hypodermic needle |
| 309 | cap |
| 310 | cap seal |
| 311 | female socket |
| 312 | guidance track |
| 313 | receiving aperture |
| 314 | -- not used -- |
| 315 | buttress surface |
| 316 | syringe body aperture |
| 317 | retainer barb |
| 318 | cap retention feature |
| 319 | syringe body retention feature |
| 320 | cap gripping feature |
| 321 | plug |
| 322 | medicament containment chamber |
| 323 | retainer flange |
| 324 | retainer flange proximal surface |
| 325 | retainer flange distal surface |
| 326 | beveled end of hypodermic needle |
| 327 | hollow protrusion |
| 328 | retainer neck |
| 329 | retainer annular securement feature |
| 330 | lower dynamic seal securement feature |
| 331 | nose aperture |
| 332 | proximal end of hypodermic needle |
| 333 | lower dynamic seal aperture |
| 334 | syringe body retaining surface |
| 335 | syringe graduation markings |
| 336 | viewing window |
| 337 | nose annular ring |
| 338 | syringe body annular groove |
| 339 | tapered seal surface on nose |

-continued

INDEX OF REFERENCE NUMERALS

| Reference | Element |
|---|---|
| 340 | tapered sealing surface on syringe body |
| 341 | seal feature on nose |
| 342 | dynamic seal annular ribs |
| 400 | fluid transfer mechanism |
| 500 | fill nozzle |
| 600 | push rod |
| 700 | syringe |
| 701 | button |
| 702 | button retainer seal |
| 703 | button retainer |
| 704 | latch |
| 705 | label |
| 706 | needle insertion/fluid injection spring |
| 707 | plunger rod |
| 708 | spring rest |
| 709 | coupler |
| 710 | inner housing |
| 711 | inner housing cap |
| 712 | dynamic seal |
| 713 | outer housing |
| 714 | fluid medicament |
| 715 | medicament container |
| 716 | hypodermic needle |
| 717 | cap |
| 718 | retraction spring |
| 719 | needle seal |
| 720 | cap plug |
| 721 | inner housing buttress surface |
| 722 | spring rest bearing surface |
| 723 | inner housing bore |
| 724 | latch retaining feature |
| 725 | plunger rod resting surface |
| 726 | button retainer slot |
| 727 | button arm |
| 728 | slot tip |
| 729 | slot buttress surface |
| 730 | gripping surface |
| 731 | graphics |
| 732 | button retainer snap fit feature |
| 733 | outer housing snap fit feature |
| 734 | cam |
| 735 | latch finger |
| 736 | syringe buttress surface |
| 737 | rib shoulder |
| 738 | proximally-disposed interior surface of syringe body |
| 739 | distal end of inner housing |
| 740 | distal opening of inner housing |
| 741 | outer housing counterbore shoulder |
| 742 | proximal surface of latch |
| 743 | distal surface of button retainer |
| 744 | annular ring |
| 745 | receiving groove |
| 746 | hinge |
| 747 | cap plug body |
| 748 | female socket |
| 749 | proximal opening of hypodermic needle |
| 750 | engaging surface of spring rest |
| 751 | outer housing bore |
| 752 | -- not used -- |
| 753 | distal surface of inner housing cap |
| 754 | sharp tip of hypodermic needle |
| 755 | outer housing distal aperture |

DETAILED DESCRIPTION

As used in this disclosure, the term "proximal" defines the end of the described embodiments opposite the hypodermic needle; that is, the axial direction opposite that of the needle. The term "distal" similarly defines the needle end of the described embodiments; that is, the axial direction towards the needle. It should also be noted that the terms "first", "second", "third", "upper", "lower", and the like may be used herein to modify various elements. These modifiers do not imply a spatial, sequential, or hierarchical order to the modified elements unless specifically stated.

Similarly, the term "enable" is hereinafter used to describe the action necessary to allow the subject of the present disclosure to advance to the next step in the usage sequence. The term "activation" is hereinafter used to describe the action necessary to cause the subject to become active, i.e. able to respond to a triggering action. The term "actuation" is hereinafter used to describe the action necessary to trigger the injection process.

Figure 1:
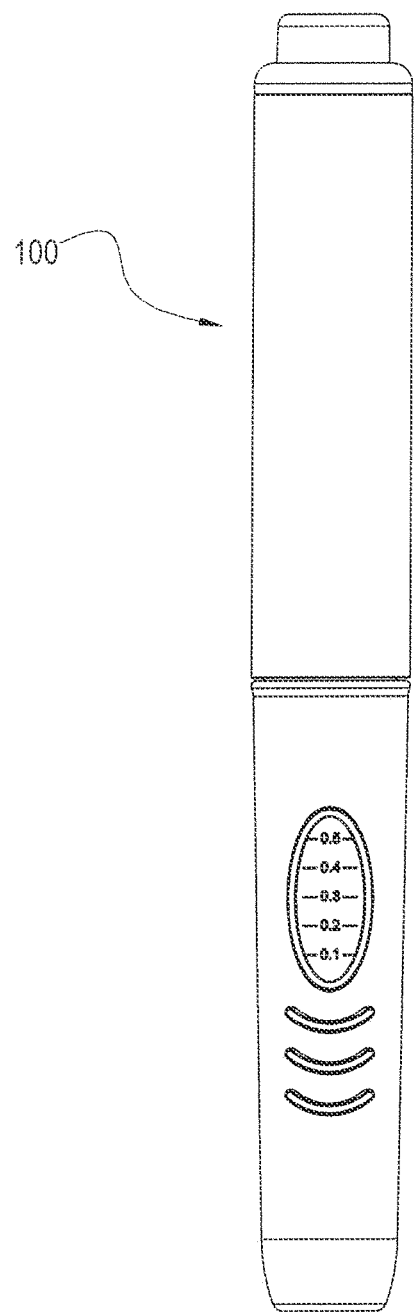
FIG. 1 is an exterior front elevation view of an exemplary embodiment of a self-retracting mechanized syringe according to the present disclosure.
Figure 6A:
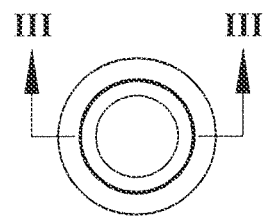
FIGS. 6A and 6B show a cross sectional view of the fully assembled automatic injection and retraction syringe of FIG. 1 with the section taken along the long axis.
Figure 6B:
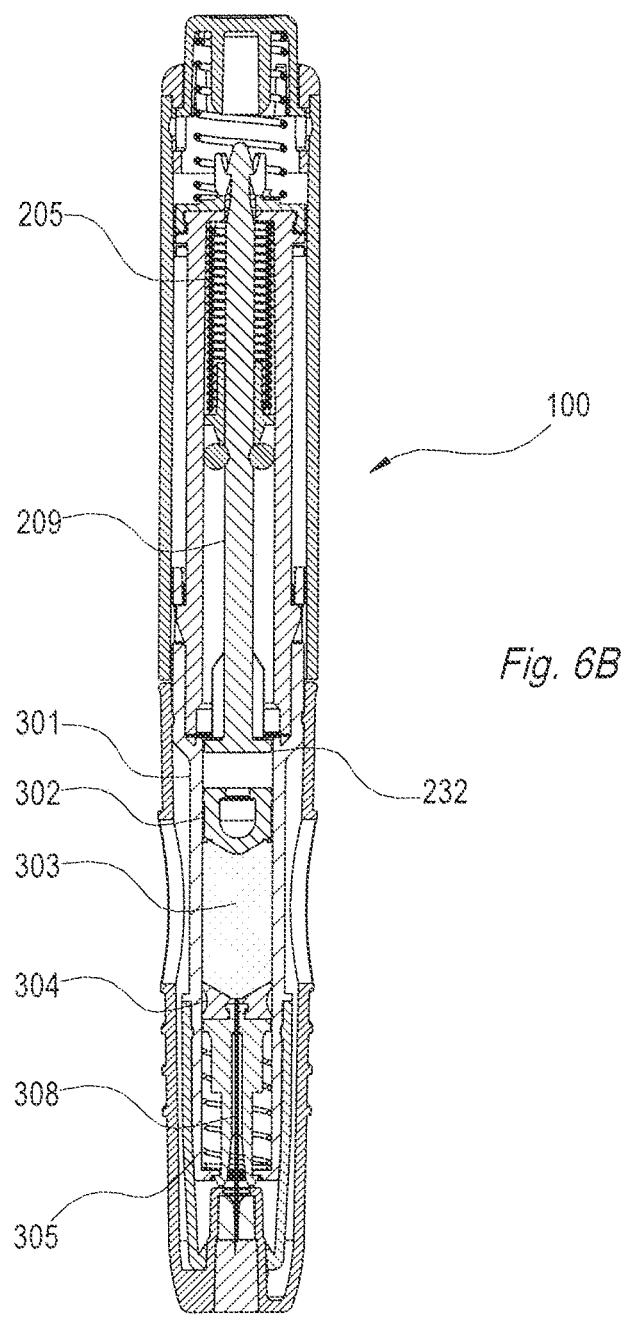

Referring to the figures and in particular to FIGS. 1 and 6, an exemplary embodiment of an automatic injection and retraction syringe 100 according to the present disclosure is shown. The automatic injection and retraction syringe 100 is generally symmetric about its long axis. Upon actuation, the automatic injection and retraction syringe 100 is adapted to automatically extend a hypodermic needle 308 from within the assembly into tissue at an injection site, displace the fluid medicament 303 through the hypodermic needle 308, and automatically retract the hypodermic needle 308 after the injection is completed.

A general aspect of operation of this disclosure is the relationship between the viscosity of the fluid medicament 303, the inner diameter of the hypodermic needle 308, the force applied upon the upper dynamic seal 302 by the needle insertion/fluid injection spring 205 by way of the plunger rod 209, the force applied by the needle retraction spring 305 upon the lower dynamic seal 304, and the friction force resisting movement of the lower dynamic seal 304 along the interior of the syringe body 301. The friction forces must be sufficiently low, the bore of the hypodermic needle 308 sufficiently small, the force of the needle retraction spring 305 sufficiently low as compared to the force of the needle insertion/fluid injection spring 205, and the viscosity of the medicament 303 sufficiently high so that the upper dynamic seal 302, the lower dynamic seal 304, the fluid medicament 303 and the hypodermic needle 308 will traverse distally to the end stop position before the fluid medicament 303 escapes the hypodermic needle 308.

An embodiment provides, for the convenience of assembly, two subassemblies hereinafter described as the "upper subassembly" and "lower subassembly" and are assembled to complete the automatic injection and retraction syringe 100. Other assembly strategies are allowable within the scope of the claims. Referring to FIGS. 2 and 4, an embodiment of the upper subassembly 200 is described. The upper subassembly 200 comprises a trigger preferentially embodied as a button 201, a sleeve cap 202, a button return spring 203, a latch 204, a needle insertion/fluid injection spring 205, a housing 206, a spring rest 207, a coupler 208, a plunger rod 209, and a sleeve 210. Upon assembly of the upper subassembly 200, the needle insertion/fluid injection spring 205 resides in a state of substantially full compression, axially coincident with and exterior to the plunger rod 209. The needle insertion/fluid injection spring 205 is confined axially on one end by a distally disposed interior surface of the housing 206, and at the opposite end by a proximally disposed surface on the spring rest 207. Referring to FIGS. 4 and 7E, latch 204 provides, preferably, a plurality of latch finger 220. Latch finger 220 provides a latch shoulder 221 that engages with a plunger rod shoulder 222 disposed on the plunger rod 209, and thereby retains the needle insertion/fluid injection spring 205 in an energized state until engagement between the plunger rod 209 and the latch 204 is defeated by the button 201. In one embodiment, the latch 204 and the housing 206 are separate components. The two components may be consolidated into a single component in an alternative embodiment. As will be more particularly described below, while referring to FIG. 11, an embodiment of the housing 206 provides male snap fit feature 233 allowing for permanent physical attachment, for example by interference snap fit engagement, with the lower subassembly 300.

Referring to FIGS. 4 and 9, spring rest 207 resides in contact with at least one coupler 208 that engages radially with a corresponding retaining feature disposed on the plunger rod 209. In an embodiment, the coupler 208 comprises a sphere. Upon assembly of the upper subassembly 200, the coupler 208 remains trapped radially between a retaining feature, which may be, for example, a groove 231 disposed upon the exterior surface of the plunger rod 209, and the bore 226 of the housing 206.

Figure 11:
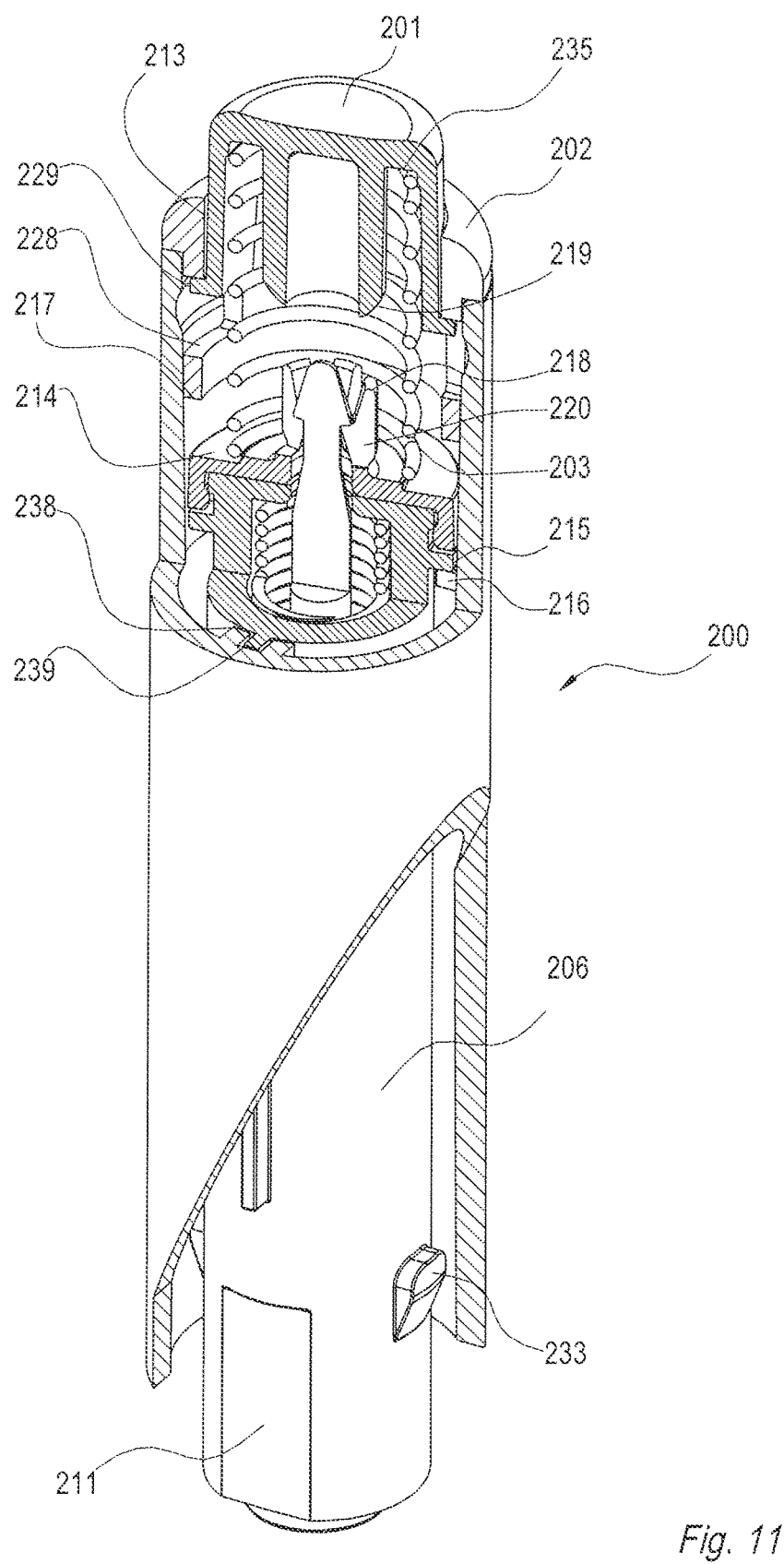
FIG. 11 shows a partial cutaway perspective view of, and further details of upper subassembly 200.

In an embodiment, and as illustrated in FIGS. 4, 7 and 11, the trigger means is embodied in the form of a button 201. The button 201 is retained in an axial sliding fit relationship within the sleeve cap 202 with a portion of the button 201 protruding proximally through an aperture 213 in the sleeve cap 202. The sleeve cap 202 is permanently secured to proximal end of the sleeve 210. Means of securement may be accomplished, for example, by interference fit or snap fit. Disposed on the button 201 and oriented in the distal direction is an unlatching feature, such as a protrusion acting as a cam 219 responsible for engaging with latch finger 220 of latch 204 to force the latch finger 220 radially outward upon the application of force upon the button 201 in the distal direction. In an alternative embodiment of the present disclosure, the button 201 as an independent component is eliminated and the distally-disposed cam 219 that cooperates with the latch 204 is incorporated as an integral element of the sleeve cap 202. These two alternative embodiments for actuating the injection sequence will be described in further detail below while referencing FIGS. 7 and 8.

Continuing with FIGS. 4 and 7, a button return spring 203 resides internally to the button 201 in a partially biased state confined on the proximal end by a distally disposed surface 235 on the button 201. The distal end of the button return spring 203 is confined by a proximally disposed face 214 on the latch 204. As will be described in greater detail while referencing other figures below, the button return spring 203 also serves to urge the sleeve 210 and the sleeve cap 202 in the proximal direction. Also while referencing other figures below, proximal travel of the sleeve 210 under influence of the button return spring 203 is limited by axial interference with a cooperating feature disposed on the exterior of the housing 206. After final assembly of the automatic injection and retraction syringe 100, application of distally applied force on the sleeve 210 while the housing 206 is held stationary causes the sleeve 210 to travel distally relative to the housing 206 and further biases the button return spring 203. The button return spring 203 thus serves two functions; it urges the button 201 proximally and also the sleeve 210 proximally. The sleeve 210 also serves as a hand grip during use of the automatic injection and retraction syringe 100. More detail regarding the sleeve 210 and the button 201 functionality, interdependency, and embodiment options will be described in further detail below while referencing other figures.

Referring to FIG. 5, the lower subassembly 300 of the present disclosure comprises a syringe body 301, an upper dynamic seal 302, a lower dynamic seal 304, a needle retraction spring 305, a retainer 306, a nose 307, a hypodermic needle 308, a cap 309, and a cap seal 310. The cap 309 may include a female socket 311, preferably dimensioned to be compliant with what is known to those skilled in the art as a female Luer taper, disposed distal to the cap seal 310. Referring to FIG. 22, preferably, installation of the fluid liquid medicament 303 into the fully-assembled automatic injection and retraction syringe 100 may be accomplished by engaging a fluid transfer mechanism 400, for example a syringe with a male Luer slip end, with the female socket 311 in a fluid tight taper lock relationship, and transferring the fluid from the fluid transfer mechanism 400 into the drug containment chamber, herein defined for the present embodiment as the space interior to the syringe body 301, proximal to the lower dynamic seal 304, and distal to the upper dynamic seal 302, as shown in the figures via the hypodermic needle 308. Referring to FIG. 23, pursuant to an alternative method of filling the automatic injection and retraction syringe 100 with fluid medicament 303, the upper subassembly 200 and lower subassembly 300 may be provided as separate subassemblies. The medicament 303 may be installed by gravity filling into the syringe body 301 of the lower subassembly 300 proximal to the lower dynamic seal 304, and thereafter installing the upper dynamic seal 302. Various methods for gravity filling and seal installation are well known to those skilled in the art. As illustrated in FIG. 6, once the fluid medicament 303 and the upper dynamic seal 302 are installed, the lower subassembly 300 is permanently secured to the upper subassembly 200 to form the automatic injection and retraction syringe 100.

Figures 7A, 7B:
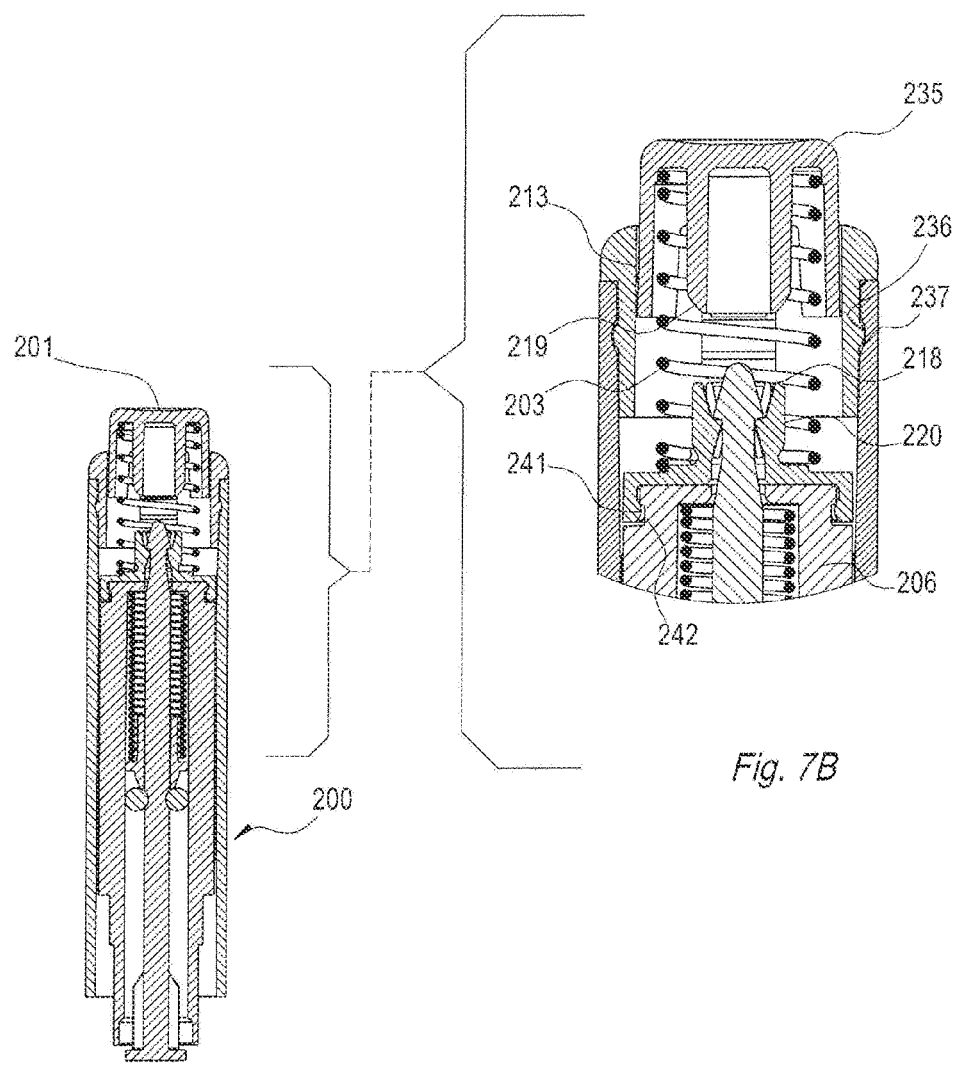

Referring to FIGS. 4, 7, 8 and 11, two embodiments of a trigger means are described. FIG. 7 illustrates a cross sectional view of the upper subassembly 200 in a first embodiment. The upper subassembly 200 and its constituents are, preferably and generally, of annular geometry symmetric about the long axis. In this embodiment, the trigger means assumes the form of a button 201 retained within the sleeve cap 202. A portion of the button 201 protrudes proximally through aperture 213 in the sleeve cap 202. The aperture 213 is sized to provide radial clearance in relation to the button 201, allowing for free axial movement of the button 201. Referring to FIG. 11, a means to limit axial travel of the button 201 within the sleeve cap 202 is provided via at least one window 228 provided on the sleeve cap 202 and at least one cooperating arm 229 provided on the button 201. The button arm 229 is dimensioned to allow restricted axial travel within the sleeve cap window 228 thus limiting axial travel of button 201 within the sleeve cap 202. The button 201 is urged in the proximal direction through contact with the button return spring 203 which is retained in a partially biased condition with its opposite end resting upon the exterior proximally disposed face 214 of the latch 204. The sleeve cap 202 and the sleeve 210 are axially aligned and permanently affixed together. Preferably, securement is provided by interference fit or snap fit. Referring to FIG. 7b, one preferred embodiment of snap fit arrangement describes male snap fit feature 236 of sleeve cap 202 and corresponding female snap fit feature 237 of the sleeve 210. Referring back to FIG. 11, the sleeve 210 is preferably configured with internally disposed sleeve ribs 238 which cooperate in an axial sliding fit relationship with corresponding longitudinal rib 239 disposed along the exterior of the housing 206. Sleeve ribs 238 in cooperation with housing rib 239 allow for free axial movement of the sleeve 210 in relation to the housing 206 while retaining the sleeve 210 in an axially coincident relationship with housing 206. This cooperative relationship between sleeve ribs 238 and housing ribs 239 also serves to prevent axial rotation of the sleeve 210 in relation to the housing 206.

Referring to FIGS. 4 and 11, a housing annular flange 215 and the sleeve retaining feature 216 cooperate to limit the proximal movement of the sleeve 210 under the influence of the button return spring 203. The sleeve retaining feature 216 is preferably smaller in diameter than the diameter of the housing annular flange 215. Thus the proximally-disposed surface of the sleeve retaining feature 216 impinges upon the distally-disposed surface of the housing annular flange 215 under the influence of the button return spring 203. Upon application of force upon the sleeve 210 in the distal direction with the automatic injection and retraction syringe 100 abutting a surface at the syringe's distal end, e.g. the injection site; the sleeve 210 is free to move distally a set distance defined as the offset distance from the sleeve cap shoulder 217 to the proximally disposed face 214 of the latch 204. Preferably, the axial travel distance allowed the button arm 229 within the sleeve cap window 228 is less than the distance between the proximally disposed tip 218 of latch finger 220 and distally disposed cam 219, thus making inadvertent contact between the button 201 and the latch 204 impossible unless the sleeve 210 is moved in a distal direction relative to the housing 206. The foregoing dimensional relationships between the button 201, the latch 204, the sleeve 210, the sleeve cap 202 and the housing 206 facilitate a safety utility, whereby actuation of syringe automatic injection and retraction 100 can only be accomplished by the combination of distal movement of the sleeve 210 relative to the housing 206 and distal movement of button 201 relative to the sleeve cap 202.

Again referring to FIGS. 4 and 7b through 7E, the distally disposed cam 219 of the button 201 cooperates with the proximally disposed latch 204. Preferably, the latch 204 provides a plurality of proximally disposed, semi-rigid latch finger 220 radially arrayed about the axis of latch 204. The button 201 and the latch 204 are preferably configured in a concentric relationship sharing the long axis of the automatic injection and retraction syringe 100. A top view of the latch 204 in the normal state is shown above FIG. 7D. Referring to FIG. 7C, a latch shoulder 221 provides a proximally disposed resting surface for distally disposed plunger rod shoulder 222. As illustrated in FIG. 7D, upon axial movement of the sleeve 210 from a first, proximal position to a second distal position, cam 219 approximates the proximally disposed tip 218 of latch finger 220. The cam 219 is configured to engage a radially inwardly disposed point at the proximally disposed tip 218 of the latch finger 220. As illustrated in FIG. 7E, further distal movement of the button 201 causes the cam 219 to engage the latch finger 220 and lever the latch finger 220 radially outward in a defined manner about a fulcrum point 223 and disengage the latch shoulder 221 from the plunger rod 209. A top view of the latch 204 in the open state is shown above FIG. 7E. Preferably, the latch 204 is comprised of material of sufficient resiliency to allow for elastic deformation of the latch finger 220 during assembly with the plunger rod 209 while also providing sufficient rigidity to support the plunger rod 209 under the force of the energized needle insertion/fluid injection spring 205 indefinitely without buckling or yielding under compressive load. One such material may be, preferentially, polycarbonate.

Referring to FIG. 7B, the latch 204 is preferable coupled to the housing 206 by way of snap fit engagement. A latch snap fit feature 241 engages with corresponding latch snap fit receiver feature 242 disposed on the housing 206.

Referring to FIG. 8, a second embodiment of the upper subassembly 200 is described. In this embodiment, the cam 219 is incorporated into an alternative embodiment of the sleeve cap 224. Other cooperative relationships between the sleeve 210, the alternative sleeve cap 224, the button return spring 203, the housing 206, the latch 204, the plunger rod 209 the needle insertion/fluid injection spring 205, the spring rest 207 and the coupler 208 remain as previously defined. Thus in this embodiment, and as illustrated in FIG. 8C, no activation function is afforded; automatic injection and retraction syringe actuation is accomplished solely by distal axial movement of the sleeve 210 relative to the housing 206 once the automatic injection and retraction syringe 100 is enabled by removing the cap 309.

Figures 9A, 9B:
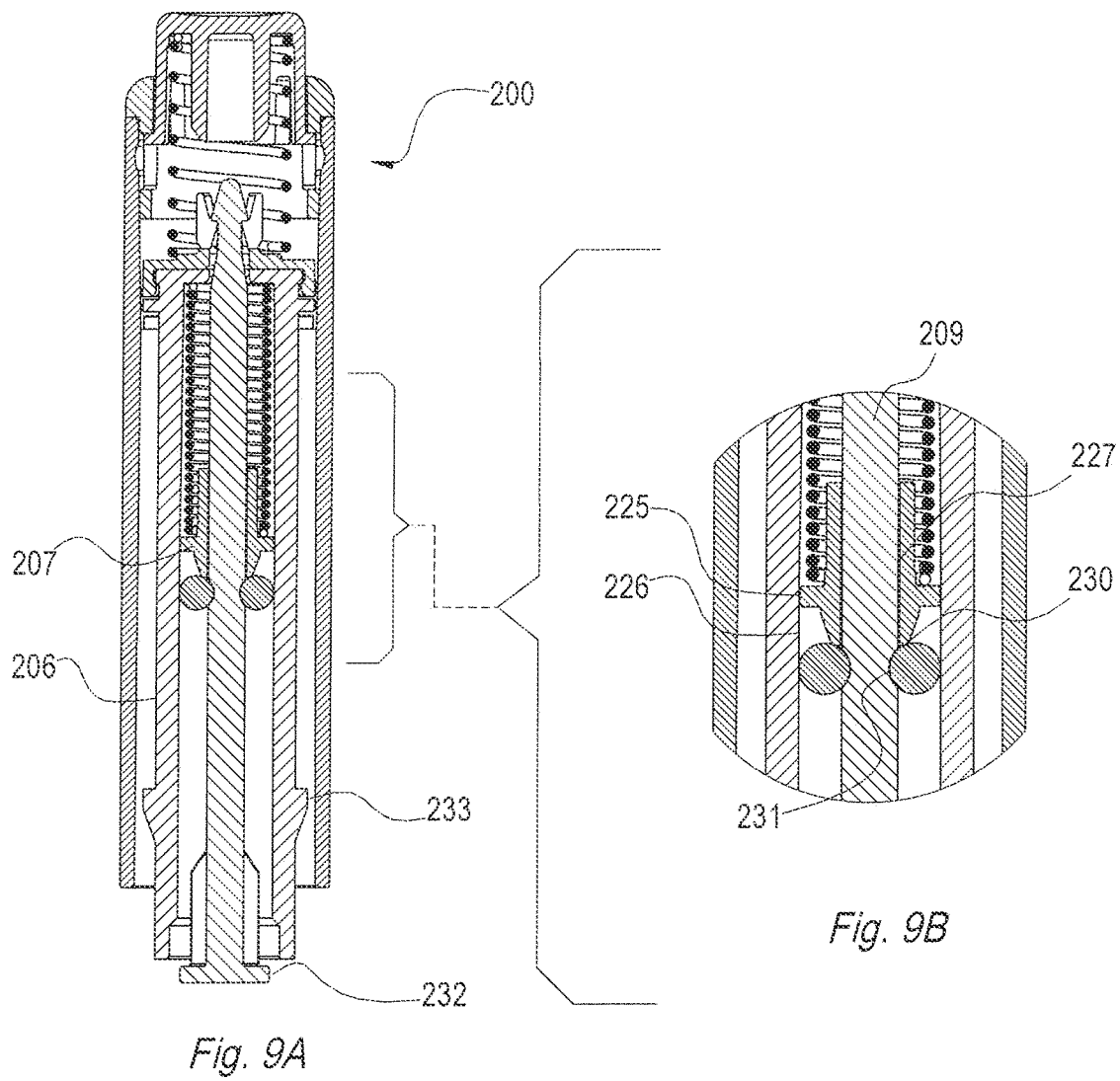
FIGS. 9A and 9B show further details of the middle region of the upper subassembly common to embodiments described in FIGS. 2, 4, 7 and 8.

Referring to FIGS. 4 and 9, an embodiment of the upper subassembly 200 and more particularly the disengageable coupling relationship between the needle insertion/fluid injection spring 205 and the plunger rod 209 is further detailed. A generally annular spring rest 207 resides within the interior bore 226 of the housing 206 and exterior to plunger rod 209. Referring to FIG. 9B, a spring rest flange 225 is disposed about the perimeter of the spring rest 207 and is dimensioned for axial sliding fit with the housing bore 226. The spring rest bore 227 is sized for an axial sliding fit with the plunger rod 209. Preferably, the spring rest 207 is comprised of material of sufficient rigidity to indefinitely survive the strain imposed by the force of the fully energized needle insertion/fluid injection spring 205 without yielding under compressive load. One such material may be, for example, polycarbonate. The distal end of the needle insertion/fluid injection spring 205 abuts against a proximally facing surface of the spring rest flange 225. The distal end of the spring rest 207 provides an annular engaging surface 230 which impinges upon the coupler 208. The preferably spherical coupler 208 resides within a plunger rod groove 231 of compatible geometry disposed upon the exterior of the plunger rod 209. The spring rest 207 and the coupler 208 thus provide an indirect relationship between the needle insertion/fluid injection spring 205 and the plunger rod 209 whereby connectivity between the needle insertion/fluid injection spring 205 and the plunger rod 209 is maintained so long as the coupler 208 remains engaged with plunger rod groove 231. The coupler 208 and the plunger rod groove 231, once assembled, are dimensioned to provide a sliding fit between the coupler 208 and the housing bore 226. So long as the coupler 208 remains engaged with plunger rod groove 231 and within the housing bore 226, the coupler 208 is trapped in engagement with the plunger rod 209. The point of contact between the annular engaging surface 230 of the spring rest 207 and the coupler 208 resides slightly radially inward from the distal-most surface of coupler 208. Thus, under the influence of energized needle insertion/fluid injection spring 205, the spring rest 207 imposes a major force component upon the coupler 208 in the distal direction and a minor force component directed radially outward.

Referring to FIGS. 4, 6 and 9, the distal end of the plunger rod 209 preferably provides a plunger rod flange 232 dimensioned to provide an easy running fit with the interior diameter of the syringe body 301 and end-to-end engagement with proximal surface of the upper dynamic seal 302.

Referring to FIGS. 9 and 10, an embodiment of the housing 206 provides a plurality of male snap fit feature 233 disposed about the exterior of the housing 206. An embodiment of the syringe body 301 provides an internally disposed guidance track feature 312 configured to accommodate and provide an axial pilot for male snap fit feature 233 to assure radial alignment with the receiving aperture 313 disposed on syringe body 301. The syringe body 301 or the housing 206, or both, are preferably comprised of a resilient material capable of elastic deformation sufficient to allow radial deflection exceeding the radial interference between the mating snap fit feature 233 and the syringe body 301 during axial engagement of the housing 206 and the syringe body 301 during final assembly of the automatic injection and retraction syringe 100. Referring to FIG. 11, preferably, the housing 206 provides a relief 211 adjacent to the male snap fit feature 233 to accommodate annular inward deflection of the syringe body 301 during the snap fit process.

Referring to FIG. 10B, the syringe body 301 also provides a radially inwardly disposed retaining surface 334 configured to receive and retain the coupler 208 upon disengagement from the plunger rod 209.

Referring back to FIGS. 5 and 10, the lower subassembly 300 comprises a syringe body 301, an upper dynamic seal 302, a lower dynamic seal 304, a needle retraction spring 305, a retainer 306, a nose 307, a hypodermic needle 308, a cap 309 and a cap seal 310. The syringe body 301, the upper dynamic seal 302 and the lower dynamic seal 304 are comprised of materials compatible with the fluid medicament 303. The hypodermic needle 308 is permanently secured to the retainer 306 in a coaxial relationship and a defined needle protrusion length. Securement is accomplished, for example, by insert molding, adhesive bonding or the like. Referring to FIG. 10C, the proximal end 332 of the hypodermic needle 308 is disposed within seal aperture 333 provided by the lower dynamic seal 304 and is configured to provide fluid communication from the medicament containment chamber 322, to the open proximal end 332 of the hypodermic needle 308. The retainer 306 is permanently affixed on its proximal end to the lower dynamic seal 304. Retention may be facilitated, preferably, by inclusion of retainer annular securement feature 329 radially disposed about the exterior of the retainer 306 and a geometrically similar lower dynamic seal securement feature 330 radially disposed within the interior of the lower dynamic seal 304. The retainer 306 provides a retainer flange 323 with a proximal surface and a distal surface. The proximal flange surface 324 of the retainer 306 approximates or contacts the distal surface of the lower dynamic seal 304 and the distal flange surface 325 of the retainer flange 323 provides a contact surface for the needle retraction spring 305 to act upon. The length of the retainer 306 from the distal flange surface 325 to the retainer barb 317 is defined to establish and sustain a partially biased condition of the needle retraction spring 305 with a known force in its free state. The upper dynamic seal 302 and the lower dynamic seal 304 are geometrically and materially configured to provide sufficient compressive interference with the interior surface of the syringe body 301 to assure static and dynamic fluid containment yet exhibit low dynamic frictional properties during axial movement. The lower dynamic seal 304 and the syringe body 301 are configured to assure friction force between the lower dynamic seal 304 and the syringe body 301 is less than the force imposed on the lower dynamic seal 304 via the retainer 306 by the partially biased needle retraction spring 305. Thus in a free condition, the lower dynamic seal 304 is urged into a fixed, proximal position relative to the syringe body 301 defined by the aforementioned length restriction posed by the retainer 306.

Again referring to FIGS. 5 and 10B, an embodiment of the upper dynamic seal 302 is preferably comprised of elastomeric or semi-elastomeric material, e.g. butyl rubber, fluorinated ethylene propylene, silicone, etc. Annular ribs 343 of upper dynamic seal 302 are configured to minimize friction in sliding contact with the interior of syringe body 301 while preventing leakage of medicament or ingress of microorganisms.

Referring to FIG. 10C, the needle retraction spring 305 resides internal to the syringe body 301 and externally coincident to the retainer 306. The proximal end of the needle retraction spring 305 impinges upon a distally disposed surface 325 of the retainer flange 323; the distal end of the needle retraction spring 305 rests against a proximally facing buttress surface 315 disposed on the distal end of the syringe body 301. The syringe body aperture 316 is sized to provide clearance for an axial slip fit with the neck 328 of the retainer 306. The retainer 306 preferably provides a plurality of distally disposed, radially deflectable retainer neck 328 symmetrically configured in an opposite hand relationship about the axis of the retainer. The retainer neck 328 exhibits sufficient resiliency to deflect radially inward into a "closed" condition upon application of a radially inward applied force. A distally tapered retainer barb 317 is disposed at the end of retainer neck 328 and is dimensioned to pass through the syringe body aperture 316 in the distal direction as retainer neck 328 deflects inwards and becomes biased to the closed condition during distal movement of the retainer barb 317 through the syringe body aperture 316. As the retainer barb 317 exits the distal end of the syringe body aperture 316, the retainer neck 328 reflexes outwardly. The retainer barb 317 is sized and geometrically configured to be prevented from reentering the syringe body aperture 316 under force imposed upon the retainer 306 in the proximal direction by the biased needle retraction spring 305, and while retainer neck 328 is in a relaxed state. The retainer neck 317 therefore remains exterior to the distal end of the syringe body 301. The retainer 306 functions as securement for the hypodermic needle 308; travel stop for proximal travel of the lower dynamic seal 304 under influence of the needle retraction spring 305; and axial guidance to maintain a coaxial alignment of the hypodermic needle 308 with the automatic injection and retraction syringe 100 during distal movement of the hypodermic needle 308.

Referring to FIGS. 10 and 21, an embodiment of the syringe body 301 provides graduation markings 335 on the exterior of the syringe body 301 indicating the volume of the fluid medicament 303. Preferably, graduation markings are provided in a known and repeatable axial and radial position. The cap 309 provides at least one viewing window 336 in a cooperative location relative to graduation marking 335. The viewing window 336 allows visualization of the contents of automatic injection and retraction syringe 100 once filled with the fluid medicament 303. The cap 309 provides at least one retention feature 318 which cooperates with a geometrically similar retention feature 319 disposed on the syringe body 301 to create a separable retaining engagement. The retaining engagement is defeated by the application of a known and predictable axial force applied distally to the cap 309 while holding the sleeve 210 stationary. While the cap 309 is engaged with the syringe body 301, the sleeve 210 cannot be caused to move in the distal direction. One utility of the cap 309 is thus a safety feature making it impossible to activate or actuate the automatic injection and retraction syringe 100 unless the cap 309 is first removed. Thus removal of the cap 309 enables the automatic injection and retraction syringe to be activated and/or actuated. Also, while the cap 309 remains engaged with the syringe body 301, radial movement of the cap 309 relative to the syringe body 301 is inhibited. This radially-retained relationship between the cap 309 and the syringe body 301 serves to establish the radial relationship between the viewing window 336 and the graduation markings 335, preferably to allow the graduation markings 335 to be seen through the viewing window 336. Referring to FIGS. 10C and 21, the preferred embodiment of the cap 309 provides a plurality of gripping feature 320 disposed about the exterior of the cap 309 to facilitate manual removal of the cap 309.

Referring to FIG. 10C, an embodiment comprises a nose 307 permanently affixed to the syringe body 301, preferably via interference snap fit and sealed relationship. An annular groove 338 is radially disposed about the periphery of the syringe body 301 and configured to cooperate with an annular radial ring 337 of similar geometry inwardly disposed about the interior surface of the nose 307. A radially disposed and tapered sealing surface 339 on the interior of the nose 307 and corresponding radially disposed and tapered sealing surface 340 on the exterior of the syringe body 301 are provided. The syringe body annular groove 338 is offset axially slightly in the distal direction in relation to radial ring 337 disposed on the nose 307 to urge the nose 307 proximally in relation to the syringe body 301 and secure tapered sealing surfaces 339 and 349 into separable annular sealing contact.

Continuing with reference to FIGS. 5 and 10C, an embodiment of the cap 309 provides an internal, annular, proximally disposed, hollow protrusion 327. The proximal end of the hollow protrusion 327 closely approximates the distal surface of the retainer 306, thus impeding the distal movement of the retainer 306, the hypodermic needle 308, and the lower dynamic seal 304, so long as the cap 309 remains engaged with the syringe body 301. The internal diameter of the hollow protrusion 327 is configured to accommodate a cap seal 310 which seals against a portion of the exterior surface of hypodermic needle 308 proximal to the beveled end 326 of the hypodermic needle 308. The cap seal 310 provides a slide able, liquid-tight interface with the exterior surface of hypodermic needle 308 and a permanently secured, non-sliding sealing engagement with a portion of the interior surface of hollow protrusion 327. An embodiment of the lower subassembly 300 provides a separable annular interference fit between the hollow protrusion 327 and a radially and proximally disposed seal feature 341 of the nose 307. The seal feature 341 engages with the exterior surface of hollow protrusion 327 in a separable interference and sealing relationship. By virtue of the sealing relationship described above and the sealed relationship between the syringe body 301 and the nose 307 described previously, the interior volume of the nose is isolated from the exterior environment until the cap 309 is removed.

Again referring to FIG. 10C, the cap 309 further provides a preferably frustroconical female socket 311 preferably compliant with the general dimensional specifications for a female Luer taper. Female socket 311 is disposed distal to the open distal end of the hypodermic needle and in fluid communication therewith. The base of the frustroconical cone is disposed in the distal direction. A plug 321 configured to engage female socket 311 in a taper lock relationship may be provided. The plug 321 preferably comprises an elastomer or provides an elastomeric constituent within a rigid exterior shell.

FIGS. 12 through 20 describe the operational sequence of the first embodiment of the automatic injection and retraction syringe 100, and particularly noteworthy states or transitional states in the operational sequence. As described and illustrated previously, a second embodiment not shown in the following sequential illustrations comprises an alternative sleeve cap 224 that eliminates the activation step and facilitates actuation solely through distal movement of the sleeve 210 in relation to the housing 206.

FIG. 12 is a cross-sectional view of the automatic injection and retraction syringe 100 filled with the fluid medicament 303 and ready for deployment.

FIG. 13 illustrates removal of the cap 309. The cap 309 is shown partially removed in FIG. 13A and fully removed in FIG. 13B. Removal of the cap 309 is facilitated by gripping the sleeve 210 with one hand, the cap 309 with the other hand, and exerting a force in the axial, distal direction upon the cap 309 while holding the sleeve 210 stationary. Removal of the cap 309 exposes the nose aperture 331 through which the hypodermic needle 308 may be subsequently extended and retracted.

FIG. 14 illustrates the automatic injection and retraction syringe 100, less the cap 309, transitioning to the activated state. FIG. 14A shows the state prior to activation;

FIG. 14B describes the state after activation. The automatic injection and retraction syringe 100 with the cap 309 removed is activated by directing the nose 307 against the injection site while grasping the sleeve 210. Application of force upon the sleeve 210 in the distal direction while the nose 307 abuts the injection site causes the sleeve 210 to traverse in distal direction relative to the housing 206, partially biasing the button return spring 203. The cam 219 of the button 201 thereby approximates the latch finger 220 as described previously.

FIG. 15 shows the automatic injection and retraction syringe 100, less the cap 309, transitioning from the activated state to the actuated state. FIG. 15A describes the state wherein the user has placed the nose 307 against the injection site and applied sufficient force upon the sleeve 210 to cause the sleeve 210 to telescope distally to achieve the activated state. FIG. 15B describes the actuated state whereupon the button 201 is depressed and cam 219 has forced the latch finger 220 radially outward. The plunger rod 209 is thus released and is now free to move distally under the influence of the needle insertion/fluid injection spring 205 acting upon the spring rest 207, the spring rest 207 acting upon the coupler 208, and the coupler 208 acting upon the plunger rod 209.

FIG. 16 illustrates the automatic injection and retraction syringe 100, less the cap 309, transitioning from the actuated state as described in FIG. 16A to the state whereupon the hypodermic needle 308 is fully extended as described in FIG. 16B. Upon release of the plunger rod 209, the needle insertion/fluid injection spring 205 forces the spring rest 207, and, by virtue of the relationship previously described, the coupler 208 and the plunger rod 209, in the distal direction. The plunger rod 209 transfers spring force onto the upper dynamic seal 302. Due to the incompressible nature of the fluid medicament 303, force is transmitted from the upper dynamic seal 302 through the fluid medicament 303 to the lower dynamic seal 304 causing the lower dynamic seal 304, the retainer 306 and the hypodermic needle 308 to travel in a distal direction in tandem with the upper dynamic seal 302 and the fluid medicament 303. The needle insertion/fluid injection spring 205 in its energized state is specified to dominate the force imposed by needle retraction spring 305, thus the needle retraction spring 305 is further biased in the process. Travel continues in the distal direction until the retainer 306 contacts the proximally disposed buttress surface 315 of the syringe body 301. Once travel is terminated, the hypodermic needle 308 has been extended externally through the nose aperture 331 a predefined distance as illustrated in FIG. 16B.

FIG. 17 illustrates the automatic injection and retraction syringe 100, less the cap 309, transitioning from the needle-inserted state as described in FIG. 17A to the state whereupon the fluid medicament 303 is fully dispelled from the automatic injection and retraction syringe 100 as described in FIG. 17B. Upon termination of the travel sequence described in the previous paragraph, the lower dynamic seal 304 remains stationary. The upper dynamic seal 302, under the continued influence of the needle insertion/fluid injection spring 205 imposing a force upon the plunger rod 209 as described previously, continues movement in the distal direction. This movement causes the fluid medicament 303 to flow into and through the hypodermic needle 308 until the upper dynamic seal 302 approximates the lower dynamic seal 304 as illustrated in FIG. 16B. The fluid medicament 303 is thus moved from within the medicament containment chamber 322 into the tissue targeted for dose delivery. The spring force available from the partially biased needle insertion/fluid injection spring 205 exceeds that of the compressed needle retraction spring 305. Thus the lower dynamic seal 304, the retainer 306 and the hypodermic needle 308 remain in their distal-most position throughout delivery of the fluid medicament 303.

Figures 18A, 18B, 18C, 18D:
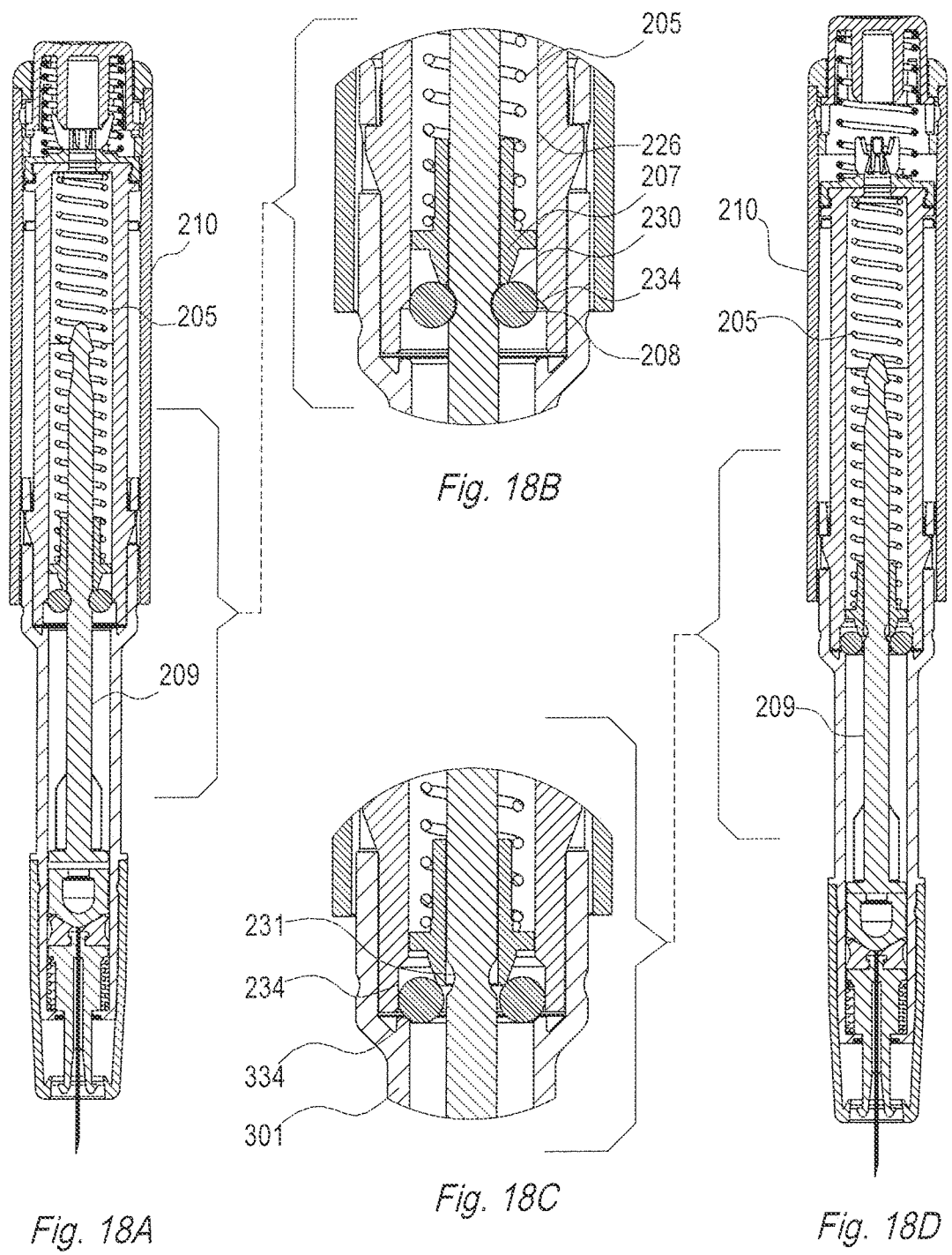

FIG. 18 illustrates disengagement of the plunger rod 209 at the end of the dose delivery. The complete mechanism is shown in FIG. 18A. Referring to FIG. 18B, as the spring rest 207 and the coupler 208 travel distally and arrive at the opening of the housing counterbore 234, the coupler 208 is no longer confined radially by the bore 226 of the housing 206. As illustrated in FIG. 18C, (a section of FIG. 18D), the annular engaging surface 230 of spring rest 207, contacting the coupler 208 on a radially interior point as previously described, urges the coupler 208 radially outward, thus disengaging the coupler 208 from involvement with plunger rod groove 231. Upon disengagement, the coupler 208 is permanently captured within the housing counterbore region 234 confined by the housing 206, the spring rest 207 and the syringe body retaining surface 334. Upon disengagement of the coupler 208 from the plunger rod groove 231, the needle insertion/fluid injection spring 205 no longer exerts any influence on the plunger rod 209.

FIG. 19 illustrates the automatic injection and retraction syringe 100, less the cap 309, transitioning from termination of the involvement of the coupler 208 and the plunger rod 209 as shown in FIG. 19A to the state whereupon the plunger rod 209, the upper dynamic seal 302, the lower dynamic seal 304, the retainer 306 and the hypodermic needle 308 have been retracted as illustrated in FIG. 19B. Upon decoupling of the coupler 208 from the plunger rod 209 as described in the previous paragraph, the energized needle retraction spring 305 exerts a proximally directed force upon the lower dynamic seal 304 via the retainer 306 sufficient to overcome the dynamic friction of the upper dynamic seal 203 and lower dynamic seal 304 in sliding contact against the interior surface of the syringe body 301. The upper dynamic seal 302 and the lower dynamic seal 304, the plunger rod 209, the retainer 306 and the hypodermic needle 308 are thus urged proximally until distal travel is terminated by the retainer barb 317 contacting the distal-most portion of the syringe body 301. Once retracted, the hypodermic needle 308 is shielded from exterior access due to the tip being retracted within the nose aperture 331 a safe distance. The hypodermic needle 308 remains permanently retracted due to continual force applied to the retainer 306 by partially biased needle retraction spring 305.

Referring back to FIG. 18*b*, at the end of its travel and after disengagement from the plunger rod 209, the spring rest 207 remains stationary in its final position, forced in the distal direction by the partially biased needle insertion/fluid injection spring 205 and restrained from further distal movement due to the coupler 208 bound against the retaining surface 334 of the syringe body 301.

Referring to FIG. 22, and as mentioned previously, one preferred method for installing the fluid medicament 303 into the automatic injection and retraction syringe 100 is accomplished by securing a fluid transfer mechanism 400, for example, a conventional Luer slip syringe as illustrated in FIG. 22A, into engagement with the female socket 311 to form a pressure tight connection as shown in FIG. 22B. Alternatively, a piston pump or peristaltic pump could be used for fluid transfer. At factory assembly and prior to filling, the upper dynamic seal 302 is positioned in close proximity to the lower dynamic seal 304. As the fluid medicament 303 is urged to flow out of the fluid transfer mechanism 400, seals established through engagement of the cap seal 310 about the hypodermic needle 308 and the taper lock engagement between the fluid transfer mechanism 400 and female socket 311 forces the fluid medicament 303 to flow into the distal end of the hypodermic needle 308. Under continued pressure imposed upon the fluid medicament 303 by the fluid transfer mechanism, fluid medicament 303 flows through the hypodermic needle 308 and enters the medicament containment chamber 322. Exploiting the low friction, dynamic sealing properties of the upper dynamic seal 302 in sliding contact with the syringe body 301, and by virtue of the buttress surface 315 preventing distal movement of the retainer 306 and lower dynamic seal 304, continued application of pressure upon the fluid medicament 303 through the fluid transfer mechanism urges the upper dynamic seal 302 in the proximal direction until the desired dose volume is transferred into the medicament containment chamber 322 as illustrated in FIG. 22C. The fluid transfer mechanism 400 is thereafter removed from engagement with the cap 309 as illustrated in FIG. 22D. Optionally, e.g. a scenario where automatic injection and retraction syringe 100 is not used immediately; the plug 321 is thereafter installed in the female socket 311 as illustrated in FIG. 22E.

Referring to FIG. 23, a second preferred method for conveying medicament into the present invention is described. The lower subassembly 300, preferably in a sterile condition, is provided absent the upper dynamic seal 302. Preferably, the lower subassembly 300, which includes pre-installed plug 321, is presented in a vertical orientation with the open, distal end of syringe body 301 disposed upwardly. As illustrated in FIG. 23A, the fluid medicament 303 is dispensed into the open end of the syringe body 301 via a fill nozzle 500 allowing gravity to carry the fluid medicament 303 into the syringe body 301. Afterwards, as illustrated in FIG. 23B, the upper dynamic seal 302 is inserted into the open bore of the syringe body 301 distal to the dose of fluid medicament 303 as, for example, using a push rod 600. Assembly of the upper dynamic seal 302 into the syringe body 301 may be, as alternative completed under low atmospheric pressure conditions. Preferably, filling of the fluid medicament 303 and placement of upper dynamic seal 302 are conducted under aseptic conditions. Several options for gravity filling of medicament and dynamic seal placement are widely known to those skilled in the art. After placement of the upper dynamic seal 302 into the syringe body 301, the upper subassembly 200 is permanently secured to the medicament-filled lower subassembly 300 to complete automatic injection and retraction syringe 100.

Referring back to the figures and in particular to FIGS. 24 through 38, an alternative embodiment of an automatic injection and retraction syringe according to the present disclosure is shown and hereinafter referred to as syringe 700. The syringe 700 is generally symmetric about its long axis. Although there are many commonalities in structure, components and function shared between the syringe 700 and the afore described embodiment of an automatic injection and retraction syringe 100, the reference numerals used to describe the alternative embodiment, its constituents and features will be shown as unique to the alternative embodiment for the purpose of distinction and clarity.

Referring to FIG. 24, syringe 700 is shown pictorially in a state wherein the medicament is onboard and syringe 700 is ready to be deployed by the user. Referring to FIG. 25, the syringe 700 is generally symmetric about its long axis. Upon actuation, the syringe 700 is adapted to automatically extend a hypodermic needle 716 from within the syringe 700 into tissue at an injection site, displace the fluid medicament 714 through the hypodermic needle 716, and thereafter retract the hypodermic needle 716 into the syringe 700. FIG. 25A is a top view of the syringe 700, showing the cross section taken and displayed as FIG. 25B.

As similarly used to describe the first preferred embodiment, a general aspect of operation of this second preferred embodiment is the relationship between the viscosity of the fluid medicament 716, the inner diameter of the hypodermic needle 716, the force applied upon the dynamic seal 712 by the needle insertion/fluid injection spring 706 by way of the plunger rod 707, the force of the retraction spring 718 upon the medicament container 715, and the friction force resisting movement of the medicament container 715 within the bore of the outer housing 713. The friction forces must be sufficiently low, the bore of the needle 716 sufficiently small, the force of the retraction spring 718 sufficiently low as compared to the force of the needle insertion/fluid injection spring 706, and the viscosity of the fluid medicament 714 sufficiently high so that the dynamic seal 712, the medicament container 715, the fluid medicament 714, and the hypodermic needle 716 will, under the influence of a released and fully energized needle insertion/fluid injection spring 706 acting upon the plunger rod 707, traverse distally to the end stop position before the fluid medicament 714 escapes the hypodermic needle 716.

Referring to FIGS. 25, 26A and 26B, an embodiment provides a self-retracting mechanized syringe 700 comprising a distally disposed trigger in the form of a button 701, a button retainer seal 702, a button retainer 703, a latch 704, a needle insertion/fluid injection spring 706, a plunger rod 707, a spring rest 708, at least one coupler 709, an inner housing 710, an inner housing cap 711, a dynamic seal 712, an outer housing 713, a medicament container 715, a hypodermic needle 716, a cap 717, a retraction spring 718, a needle seal 719, and a cap plug 720. Upon assembly of syringe 700, the needle insertion/fluid injection spring 706 resides in a state of substantially full compression, axially coincident with and exterior to the plunger rod 707. The needle insertion/fluid injection spring 706 is confined axially at one end by a distally disposed buttress surface 721 of the inner housing 710 and at the other end by a proximally disposed bearing surface 722 of the spring rest 708. The needle insertion/fluid injection spring 706 is confined radially by the bore 723 of the inner housing 710. Referring to FIG. 26B, the latch 704 provides retaining feature 724 that engages with resting surface 725 disposed about the plunger rod 707 to retain the needle insertion/injection spring 706 in an energized state until engagement between the plunger rod 707 and the latch 704 is defeated by sufficient axial force applied in the distal direction upon the button 701 while the button 701 is in the activated condition. The latch 704 and the inner housing 710 are preferably separate components but may, alternatively, be consolidated into a single component within the scope of the claims.

Referring to FIGS. 27A through 27C which further describe an alternative embodiment syringe 700, a button 701 resides with a portion exposed to the exterior of the syringe 700 and a portion interior to the syringe 700. The button 701 is captured in a coaxial relationship with and internal to the button retainer 703 and cooperates in a rotatable and axially slideable relationship with the button retainer 703. The button retainer 703 provides at least one button retainer slot 726 which cooperates with a corresponding button arm 727 radially disposed on the button 701. The button arm 727 protrudes radially sufficiently so as to nest into the button retainer slot 726. By virtue of physical interference, the button retainer slot 726 presents limitations to the movement of the button arm 727 within the button retainer slot 726. To this end, the button retainer slot 726 is configured to allow the button arm 727 to rotate about its long axis in relation to the button retainer 703 from a first rotational position as shown in FIG. 27A to a second rotational position as shown in FIG. 27B. The first position shown in FIG. 27A corresponds to a functional state wherein the button 701 is prevented from axial, distal movement and the second state shown in FIG. 27B corresponds to a functional state wherein the button 701 is allowed axial, distal movement. A slot tip 728 is disposed on the surface of the button retainer slot 726 and configured to present a slight interference to radial motion of the button 701 as it rotates from the first state to the second state. The physical properties of the button retainer 703 are preferably semi-rigid allowing deflection of the slot tip 728 as the button 701 moves from the first position to the second position. Once the button 701 is rotated into the second position, deflection of the slot tip 728 terminates and the slot tip 728 returns to its natural, unbiased condition. Once button 701 is rotated to the second position wherein the slot tip 728 is freed from contact with the button arm 727, a buttress surface 729, disposed on the slot surface, imposes a physical interference with the button arm 727 which disallows the button 701 to return from the second position back to the first position. At least one flatted and radially disposed gripping surface 730 is presented upon the button 701 providing fingertip leverage that facilitates rotating the button 701 from the first position to the second position. Once the button 701 is rotated from the first position to the second position, the button arm 727 is confined to axial movement within the button retainer slot 726; an axial, distal force applied to the button will then cause the button to translate distally from the second position shown in FIG. 27B to a third position shown in 27C.

The first position described above corresponds to a "safety on" condition of the syringe 700 in which the syringe 700 cannot be actuated; the second position described above corresponds to a "safety off" condition in which the syringe 700 can be actuated. Preferably, the button arm 727 is visible through the button retainer slot 726 which allows the visible portion of the button arm 727 to serve as a visual indicator of the "locked" vs. "unlocked" status. As described in FIG. 24, preferably, recognizable iconic graphics 731 denoting a "locked" and an "unlocked" condition are provided on the exterior surface of the syringe 700 at either end of the slot through which the button arm is visible and wherein the button arm is allowed rotational movement; the "locked" graphic being disposed adjacent to the first position and the "unlocked" graphic being disposed adjacent to the second position. Referring to FIGS. 24 and 25, graphics 731 may be incorporated into a label 705 attached about the periphery of the outer housing 713.

Referring to FIG. 26A and FIG. 26B, an elastomeric button retainer seal 702 is preferably provided. The button retainer seal 702 resides in a compressive condition interfering radially with the exterior surface of button 701 and inwardly disposed surface of button retainer 702 thereby inhibiting air exchange between the interior and exterior of the syringe 700. Button retainer seal 702 cooperates with the button 701 allowing both rotational and axial movement of the button 701 relative to the button retainer seal 702. The button retainer 703 is permanently retained within the outer housing 713 preferably by way of interference snap fit as exemplified in FIG. 26B by the button retainer snap fit feature 732 and outer housing snap fit feature 733. Alternatively, button retainer 703 may be permanently retained within the outer housing 713 by means of ultrasonic welding, solvent bonding, adhesive bonding, or other common bonding methods known those skilled in the art.

Notwithstanding the foregoing, button functionality and in particular the role of cam 734 and its relationship with latch finger 735 are as described previously in this disclosure.

Referring to FIGS. 28A and 28B, a medicament container 715, a dynamic seal 712 and a hypodermic needle 716 provide a storage compartment for the fluid medicament 714. The medicament container 715 and the hypodermic needle 716 are permanently bonded together as a subassembly with the proximal opening of the hypodermic needle 716 in open fluid communication with the interior of the medicament container 715. Bonding is preferably accomplished by way of an adhesive. Alternatively, the hypodermic needle 716 may be molded into the medicament container 715. A distal facing syringe buttress surface 736 is disposed about the periphery of medicament container 715. The medicament container 715 provides a distally facing buttress surface 736. The buttress surface 736 cooperates with a corresponding rib shoulder 737 internally and proximally disposed within outer housing 713 to arrest axial travel of medicament container 715 travelling distally under the influence of energized needle insertion/fluid injection spring 706. In addition to arresting distal travel of the medicament container 715, the rib shoulder 737 defines a datum by which the distance the hypodermic needle 716 extends beyond the distal end of syringe 700 upon actuation and subsequent needle insertion can be established and controlled. Similarly, the rib shoulder 737 establishes a known axial location of the proximally-facing interior surface 738 of the medicament container 715 in relation to the distal end 739 of the inner housing 710 to assure that the coupler 709 exits the distal end 739 of the inner housing 710 and disengages from the plunger rod 707 as the dynamic seal 712 approximates the proximally-facing interior surface 738 of the medicament container 715.

Again referring to FIG. 28B, a proximally disposed counterbore shoulder 741 disposed about the interior surface of the outer housing 713 provides a buttress surface upon which the distal end of the inner housing cap 711 resides after assembly of the syringe 700. Referring back to FIG. 26B, the proximal end of the inner housing 710 is secured axially by contact with the proximal surface 742 of the latch 704 and the distal surface 743 of the button retainer 703.

Referring to FIGS. 29A and 29B, a cap plug 720 is described. The function of cap plug 720 is as described previously herein and in function is comparable to the plug 321, i.e. it serves to close the distal end of the syringe 700 once the fluid medicament 714 is conveyed into the medicament container 715 through the hypodermic needle 716. Preferably, the elastomeric or semi-elastomeric cap plug 720 is attached to the cap 717 via an annular ring 744 which when assembled with the cap 717 resides within a corresponding receiving groove 745 disposed about the periphery of the distal end of the cap 717. A flexible hinge 746 connect the cap plug body 747 to the annular ring 744 thus retaining the cap plug 720 in direct assembly with the cap 717 and allows the cap plug body 747 to swing into engagement with the female socket 748 disposed at the distal end of the cap 717.

FIGS. 30 through 35 describe the operational sequence of an alternative embodiment (syringe 700) after it has been loaded with fluid medicament and illustrate particularly noteworthy states or transitional states in the operational sequence. FIGS. 30A through 30C are cross sectional views of the syringe 700 and depict the cap 717 being removed from the filled syringe 700. FIG. 30A is a cross-sectional view of syringe 700 filled with fluid medicament 714 and ready for deployment.

FIG. 30B illustrates removal of the cap 717 effectuated by application of a distally-directed force applied upon cap 717 while holding the filled syringe 700 stationary. FIG. 30C illustrates the syringe 700 with the cap 717 removed.

FIGS. 31A through 31C illustrate the medicament-filled syringe 700, less the cap 717, as it transitions from an un-activated to activated state. FIG. 31A illustrates a portion of an exterior prospective view of the medicament-filled syringe 700 in the "locked" position. The visible surface of the button arm 727 is shown adjacent to the "locked" graphic. FIG. 31B illustrates the same exterior prospective view of the medicament-filled syringe 700 once the button 701 is rotated from the "locked" position to the "unlocked" position. By example, moving the button 701 from the "locked" to the "unlocked" position is accomplished by gripping the syringe outer housing 713 with one hand while grasping the button 701 with the thumb and forefinger of the other hand and rotating the button 701 counterclockwise about its axis from the "locked" to the "unlocked" position.

FIGS. 32A and 32B illustrate the medicament-filled syringe 700, less the cap 717, as it transitions from an activated state in which the button 701 has been moved from the "locked" to the "unlocked" position, as described above, to an actuated state in which the button 701 has been forced in the distal direction sufficiently to have the cam 734 disposed on the button 701 engage with and pry open the latch finger 735 thereby releasing the plunger rod 707.

FIGS. 33A and 33B illustrate the medicament-filled syringe 700, less the cap 717, as it transitions from the actuated state described in FIG. 32B to the state whereupon the hypodermic needle 716 is fully extended as described in FIG. 33B. Upon release of the plunger rod 707 during actuation the needle insertion/fluid injection spring 706 acts upon the spring rest 708 and, by virtue of the relationship between the spring rest 708, the coupler 709, and the plunger rod 707 described previously within this disclosure, the plunger rod 707 is driven distally and impinges upon the dynamic seal 712. As the needle insertion/fluid injection spring 706 extends and forces the plunger rod 707 in the distal direction, and due to the incompressible nature of the fluid medicament 714, the assembly comprising the medicament container 715, the dynamic seal 712, the hypodermic needle 716, and the fluid medicament 714 translate distally until the medicament container 715 abuts the proximally disposed rib shoulder 737 of the outer housing 713. As the medicament container 715 traverses this distance, and due to the relative weakness of the retraction spring 718 compared to the strength of the needle insertion/fluid injection spring 706, the retraction spring 718 compresses from a first, partially biased state to a second, more significantly biased state.

FIGS. 34A and 34B illustrate the syringe 700, less the cap 717, transitioning from the needle-inserted state as described in FIG. 34A to the state whereupon fluid medicament 714 is fully dispelled from the syringe 700 as shown in FIG. 34B. Upon termination of the travel sequence described in the above paragraph, the medicament container 715 and attached hypodermic needle 716 remain stationary. The dynamic seal 712, under the continued influence of the needle insertion/fluid injection spring 706 imposing a force upon the plunger rod 707 as described previously, continues movement in the distal direction. This movement causes fluid medicament 714 to flow into the proximal opening 749 of the hypodermic needle 716, through the hypodermic needle 716 and into the target tissue at the injection site. Flow of the fluid medicament 714 continues until the dynamic seal 712 approximates the proximally-facing interior surface 738 of the medicament container 715 as illustrated in FIG. 34b thereby effectuating dose delivery. The spring force available from the partially biased needle insertion/fluid injection spring 706 exceeds that of the compressed needle retraction spring 718 even at the end of dose delivery; the medicament container 715 thereby remains stationary at its distal-most allowable position throughout the delivery of the fluid medicament 714.

FIGS. 35A through 35D illustrate disengagement of the coupler 709 from the plunger rod 707 at the end of dose delivery. Referring to FIGS. 35A and 35B, as the spring rest 708 and the coupler 709 travel distally and exit the distal opening 740 of the inner housing 710, the coupler 709 is no longer confined radially by the bore 723 of the inner housing 710. As illustrated in FIG. 34B, the annular engaging surface 750 of the spring rest 708 contacting the coupler 709 on a radially interior point of the coupler 709 as previously described. The applied force imposed upon the coupler 709 by the spring rest 708 thus includes a radially outwardly directed force component. This outwardly directed force component urges the preferably spherical coupler 709 radially outward into contact with the bore 723 of the inner housing 710. The outwardly directed force component is a function of the sine of the contact angle measured between a line through the coupler 709 center and parallel to the long axis of the syringe 700 and a line from the coupler 709 center to the point of contact between the coupler 709 and the spring rest 708. Thus as the coupler 709 resides within the bore 723 of the inner housing 710, it remains in contact with the bore 723 of the inner housing 710, the spring rest 708, and the plunger rod 707. As the fluid medicament 714 is delivered the plunger rod 707, the spring rest 708 and the coupler 709 travel distally and in tandem along within the bore 723 of the inner housing 710. Upon arrival at the distal opening 740 of the inner housing 710, the coupler 709 escapes the bore 723 of the inner housing 710 and the radial force constituent applied upon the coupler 709 by the spring rest 708 urges the coupler 709 radially outward. As the coupler 709 begins to move radially outward under the influence of the spring rest 708, the contact angle increases thus increasing the radial component of the applied force until full separation of coupler 709 from the plunger rod 707 occurs. As illustrated in FIGS. 35C and 35D, once the coupler 709 escapes the bore 723 of the inner housing 710, the coupler 709 disengages from the plunger rod 707 and the coupler 709 becomes trapped within the inner housing cap 711. The coupler 709 thereafter remains permanently retained within the inner housing cap 711 by the spring rest 708 which remains under the influence of the partially biased needle insertion/fluid injection spring 706.

FIGS. 36A and 36B illustrate the syringe 700, less the cap 717 transitioning from termination of the involvement of the coupler 709 and the plunger rod 707 as shown in FIG. 36A to a state whereupon the plunger rod 707, dynamic seal 712, medicament container 715 and hypodermic needle 716 have been forced proximally by the energized retraction spring 718 into a retracted state as illustrated in FIG. 36B. As illustrated in FIG. 36A, the energized retraction spring 718 exerts a proximally directed force upon the medicament container 715. Upon decoupling of the coupler 709 from the plunger rod 707 as described in the previous paragraph, the needle insertion/fluid injection spring 706 no longer exerts any influence upon the plunger rod 707. Given that the medicament container 715 is preferably dimensioned for an easy running fit within the outer housing bore 751, the biased retraction spring 718 therefore urges the plunger rod 707, the dynamic seal 712, the medicament container 715 and the hypodermic needle 716 in the proximal direction until the proximal end of the medicament container 715 abuts the distal surface 753 of the inner housing cap 711 as illustrated in FIG. 36B. In this final condition, the sharp tip 754 of the hypodermic needle 716 is retracted sufficiently within the distal aperture 755 of the outer housing 713 that it is rendered inaccessible and does not thereafter represent a risk of needle stick injury.

Figures 38A, 38B, 38C, 38D, 38E:
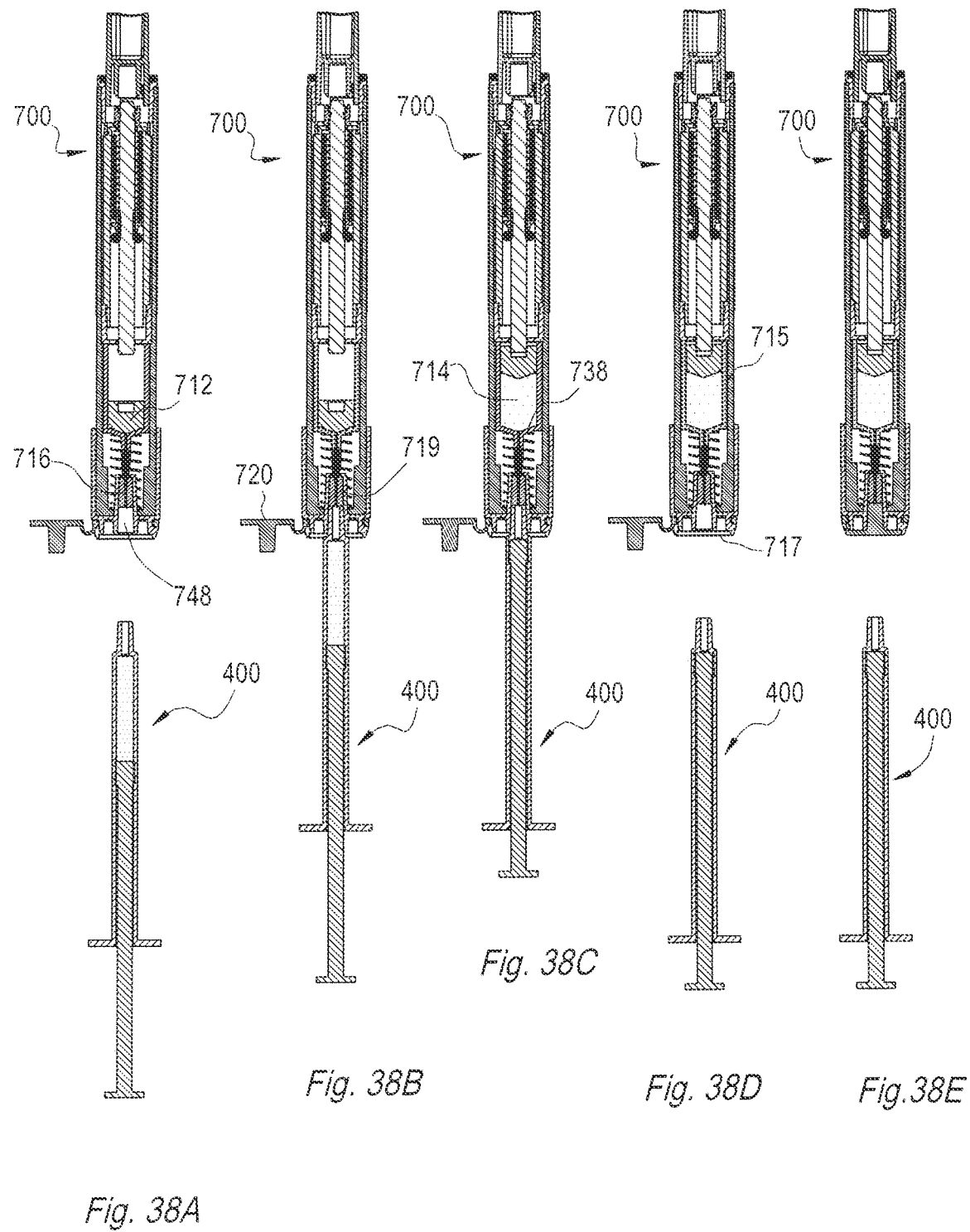

Referring to FIGS. 38A through 38E, and as similarly described in the prior embodiments; one preferred method for installing the fluid medicament 714 into the syringe 700 is accomplished by securing a fluid transfer mechanism 400, for example a conventional Luer slip syringe as illustrated in the figure, into engagement with the female socket 748 provided at the distal end of cap 717 to form a pressure tight connection as shown in FIG. 38B. Alternatively, a piston pump or peristaltic pump could be used for fluid transfer. At factory assembly and prior to filling, the dynamic seal 712 is positioned in close proximity to the proximally-facing interior surface 738 of the medicament container 715. As the fluid medicament 714 is urged to flow out of the fluid transfer mechanism 400, seals established through engagement of the needle seal 719 about the hypodermic needle 716 and the liquid tight engagement between the fluid transfer mechanism 400 and the female socket 748 forces the fluid medicament 714 to flow into the distal end of the hypodermic needle 716. Under continued pressure imposed upon the fluid medicament 714 by the fluid transfer mechanism 400, the liquid medicament 714 flows into the space between the distal end of the dynamic seal 712 and medicament container 715 via the hypodermic needle 716 in a direction opposite to that of the direction of fluid flow that occurs during dose delivery. Exploiting the low friction dynamic sealing properties of the dynamic seal 712, continued application of pressure upon the fluid medicament 714 via the fluid transfer mechanism 400 urges the dynamic seal 712 in the proximal direction until the desired dose volume is transferred into the internal volume of the medicament container 715 distal to the dynamic seal 712 and proximal to the hypodermic needle 716 as illustrated in FIG. 38C. The fluid transfer mechanism 400 is thereafter removed from engagement with the cap 717 as illustrated in FIG. 38D. Optionally, e.g. a scenario where the medicament-filled syringe 700 is not used immediately; the cap plug 720 is installed as previously described in the female socket 748 as illustrated in FIG. 38E.

None of the description in this application should be read as implying that any particular element, step, or function is an essential element which must be included in the claim scope; the scope of patented subject matter is defined only by the allowed claims. Moreover, none of these claims are intended to invoke 35 U.S.C. Section 112(f) unless the exact words "means for" are used, followed by a gerund. The claims as filed are intended to be as comprehensive as possible, and no subject matter is intentionally relinquished, dedicated, or abandoned.

The invention claimed is:

1. A method for transferring a medicinal fluid into a drug delivery device comprising:
    attaching onto the drug delivery device in a sealed relationship a fluid transfer device containing the medicament to be transferred wherein the drug delivery device is attached to the fluid transfer device by coupling a first Luer taper of the fluid transfer device with a second Luer taper of the drug delivery device;
    conveying, by application of a force to an actuator of the fluid transfer device, the medicament from the fluid transfer device into the drug delivery device, wherein the medicament is conveyed from the fluid transfer device into the drug delivery device through a hypodermic needle constituent of the drug delivery device, and wherein the hypodermic needle of the drug delivery device delivers the medicament into tissue at an injection site; and
    thereafter terminating the sealed relationship between the fluid transfer device and the drug delivery device by separating the first Luer taper and the second Luer taper.

2. A method as described in claim 1, where the drug delivery device further comprises an inlet; the method further comprising:
    plugging the inlet after the medicament is transferred into the drug delivery device and the fluid transfer device is removed from sealed connection with the drug delivery device.

3. An apparatus for injection of a liquid medicament, comprising:
    a housing;
    a drug containment chamber disposed internally to the housing and providing a volume for storage of a liquid medicament;
    a slideable piston disposed proximal to the drug containment chamber;
    a spring disposed within the housing, the spring configured to apply force upon the piston upon release of the spring;
    a releasable latch configured to selectively release the spring;
    a removable cap disposed about the housing and releasably connectable to the housing, the removable cap including an inlet exposed at an exterior of the apparatus when the apparatus is fully assembled, wherein the inlet is dimensioned to be compliant with a female Luer taper;
    a hypodermic needle including a first end in fluid communication with the drug containment chamber and a second end in fluid communication with the removable cap inlet; and
    the removable cap further providing a slideable and liquid-tight seal with the hypodermic needle.

4. A kit for preparing an apparatus for injection of a liquid medicament, the kit comprising:
    the apparatus comprising:

a housing;

a drug containment chamber disposed internally to the housing and providing a volume for storage of a liquid medicament;

a slideable piston disposed proximal to the drug containment chamber;

a spring disposed within the housing, the spring configured to apply force upon the piston upon release of the spring;

a releasable latch configured to selectively release the spring;

a removable cap disposed about the housing and releasably connectable to the housing, the removable cap including an inlet exposed at an exterior of the apparatus when the apparatus is fully assembled, wherein the inlet is dimensioned to be compliant with a female Luer taper;

a hypodermic needle including a first end in fluid communication with the drug containment chamber and a second end in fluid communication with the removable cap inlet; and the removable cap further providing a slideable and liquid-tight seal with the hypodermic needle; and a pre-filled syringe holding a liquid medicament, wherein the pre-filled syringe is dimensioned to be compliant with a male Luer taper to make a liquid-tight connection with the female Luer taper.

5. The kit of claim 4, where the liquid-tight connection is accomplished by the mating of Luer tapers.

6. The method of claim 1, wherein the actuator of the fluid transfer device is a plunger, and wherein conveying the medicament further comprises actuating the plunger of the fluid transfer device to expel the medicament from the fluid transfer device and into the drug delivery device.

7. The method of claim 1, wherein conveying the medicament further comprises reducing an internal volume of the fluid transfer device to expel the medicament from the fluid transfer device and into the drug delivery device.

* * * * *